(12) United States Patent
Noji et al.

(10) Patent No.: US 11,231,370 B2
(45) Date of Patent: Jan. 25, 2022

(54) MICROSCOPIC BODY ENCLOSING METHOD, MICROSCOPIC BODY DETECTION METHOD, AND MICROSCOPIC BODY DETECTION DEVICE

(71) Applicant: JAPAN SCIENCE AND TECHNOLOGY AGENCY, Kawaguchi (JP)

(72) Inventors: Hiroyuki Noji, Tokyo (JP); Kazuhito Tabata, Tokyo (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 341 days.

(21) Appl. No.: 16/496,197

(22) PCT Filed: Mar. 28, 2018

(86) PCT No.: PCT/JP2018/012678
§ 371 (c)(1),
(2) Date: Sep. 20, 2019

(87) PCT Pub. No.: WO2018/181443
PCT Pub. Date: Oct. 4, 2018

(65) Prior Publication Data
US 2020/0173925 A1    Jun. 4, 2020

(30) Foreign Application Priority Data

Mar. 29, 2017   (JP) .............................. JP2017-064789

(51) Int. Cl.
*G01N 21/64* (2006.01)
*G01N 1/36* (2006.01)
*G01N 21/31* (2006.01)

(52) U.S. Cl.
CPC ........... *G01N 21/6458* (2013.01); *G01N 1/36* (2013.01); *G01N 21/31* (2013.01)

(58) Field of Classification Search
CPC ...... G01N 21/6458; G01N 1/36; G01N 21/31; G01N 2021/7786; G01N 33/5436;
(Continued)

(56) References Cited

U.S. PATENT DOCUMENTS

2005/0220675 A1   10/2005  Reed et al.
2012/0196774 A1   8/2012  Fournier et al.
(Continued)

FOREIGN PATENT DOCUMENTS

CN      103008037 A    4/2013
EP      2 685 266 A1   1/2014
(Continued)

OTHER PUBLICATIONS

European Patent Office, "Extended European Search Report", issued in European Patent Application No. 18 774 733.2, which is a counterpart to U.S. Appl. No. 16/496,197, dated Nov. 20, 2020, 9 pages.
(Continued)

*Primary Examiner* — Kiho Kim

(57) ABSTRACT

Provided is a method of enclosing a microscopic body in at least some of a plurality of cavities formed in the surface of a substrate, including the step of arranging an insertion member above the cavity-formed surface of the substrate, determining relative positions of the insertion member and the substrate by a support section provided on the insertion member such that the bottom surface of the insertion member and the cavity-formed surface of the substrate face each other, thereby providing a solution introduction space between the bottom surface of the insertion member and the cavity-formed surface of the substrate, and providing a
(Continued)

solution discharge space that is in communication with the solution introduction space, the solution discharge space being located above the bottom surface of the insertion member, and between the substrate and the insertion member, within the substrate and/or within the insertion member.

21 Claims, 17 Drawing Sheets

(58) Field of Classification Search
CPC ....... B01L 2200/0605; B01L 2300/042; B01L 2300/046; B01L 2300/0829; B01L 2300/0864; B01L 2300/0893; B01L 2400/0406; B01L 3/5085; C12Q 1/34
See application file for complete search history.

(56) References Cited

U.S. PATENT DOCUMENTS

| | | |
|---|---|---|
| 2013/0345088 A1 | 12/2013 | Noji et al. |
| 2016/0202281 A1 | 7/2016 | Fang et al. |
| 2017/0176430 A1 | 6/2017 | Noji |

FOREIGN PATENT DOCUMENTS

| | | | |
|---|---|---|---|
| JP | 2004-309405 A | 11/2004 | |
| JP | 3668198 B2 * | 7/2005 | ........... G01N 21/253 |
| JP | 2014-503831 A | 2/2014 | |
| WO | 2012/121310 A1 | 9/2012 | |
| WO | 2016/006208 A1 | 1/2016 | |

OTHER PUBLICATIONS

International Search Report received for PCT Patent Application No. PCT/JP2018/012678, dated Jun. 26, 2018, 5 pages (2 pages of English translation of International Search Report and 3 pages of original International Search Report).

China National Intellectual Property Administration, "First Office Action", issued in Chinese Patent Application No. 201880021677.X, which is a counterpart to U.S. Appl. No. 16/496,197, dated Oct. 28, 2021, 8 pages (3 pages of English translation of Chinese Office Action and 5 pages of original Chinese Office Action).

* cited by examiner (A)

(B)

(C)

(D)

(E)

(F)

(G)

(A)

(B)

(A)

(B)

MICROSCOPIC BODY ENCLOSING METHOD, MICROSCOPIC BODY DETECTION METHOD, AND MICROSCOPIC BODY DETECTION DEVICE

CROSS REFERENCE TO RELATED APPLICATIONS

This patent application is a U.S. national stage application under 35 U.S.C. § 371 of International Patent Application No. PCT/JP2018/012678 filed on Mar. 28, 2018, which claims the benefit of foreign priority to Japanese Patent Application No. JP 2017-064789 filed on Mar. 29, 2017. The International Application was published in Japanese on Oct. 4, 2018, as International Publication No. WO 2018/181443 A1 under PCT Article 21(2).

TECHNICAL FIELD

The present invention relates to a microscopic body enclosing method, a microscopic body detection method; and a microscopic body detection device. More specifically, the present invention relates to a method or the like of forming droplets in which microscopic bodies are enclosed in a plurality of cavities formed separately from each other on a substrate.

BACKGROUND ART

There has been a need for a technique enabling detection of markers such as nucleic acids, proteins, viruses and cells quickly, in a simplified manner, and with high sensitivity for diagnosis of diseases, infectious diseases, etc. For example, if a marker protein (100 molecules from each cell) is secreted into 5 liters of blood from one million cancer cells contained in a tumor of 1 $mm^3$ in volume, then the blood concentration of the marker protein is about 30 aM. There has been a need for techniques that enable detection of substances of such very low concentrations.

As one of such techniques, "single molecule enzyme assay" may be mentioned, according to which substances to be detected such as nucleic acids, proteins, viruses, cells, etc. are enclosed in droplets of extremely small volume and detected by an immunological method using a labeled antibody. According to the single molecule enzyme assay, the to-be-detected substances can be detected with the sensitivity at the level of one molecule unit.

Patent Literature 1 discloses, as a technique applicable to single molecule enzyme assay, "a method of sealing beads that includes a beads introduction step of introducing a hydrophilic solvent including beads into a space between a lower layer section including a plurality of receptacles each of which is capable of storing only one of the beads and which are separated from each other by a sidewall having a hydrophobic upper surface and an upper layer section facing a surface of the lower layer section on which surface the plurality of receptacles are provided and a hydrophobic solvent introduction step of introducing a hydrophobic solvent into the space, where the hydrophobic solvent introduction step is carried out after the beads introduction step."

The technique disclosed in Patent Literature 1 uses "an array comprising a lower layer section provided with a plurality of receptacles being separated from each other by a sidewall having a hydrophobic upper surface and an upper layer section facing, via a space, a surface of the lower layer section on which surface the plurality of receptacles are provided," which involves use of an array having a flow cell structure where the lower layer section and the upper layer section face each other via a space. This technique, according to the disclosure, "makes it possible to efficiently seal a large number of beads into an array and thereby detect target molecules of low concentration with high sensitivity."

CITATIONS LIST

Patent Literature

Patent Literature 1: International Publication No. WO 2012/121310
Patent Literature 2: Japanese Patent Laid-Open No. 2004-309405

SUMMARY OF INVENTION

Technical Problem

An object, amongst other objects, of the present invention is to provide a technique for enclosing, to-be-detected substances such as nucleic acids, proteins, viruses, cells, etc. in droplets of an extremely small volume by a simple operation and enabling highly sensitive detection.

Solution to Problem

In order to solve the above-described problem, the present invention provides the following features [1] to [32].

[1] A method of enclosing a microscopic body in at least some of a plurality of cavities formed in a surface of a substrate and separated from each other, the method including:

(1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and providing a solution discharge space that is in communication with the solution introduction space, the solution discharge space being located above the bottom surface of the insertion member, and between the substrate and the insertion member, within the substrate and/or within the insertion member;

(2) a second step of introducing a first liquid into the solution introduction space, wherein the first liquid includes the microscopic body and a first solvent; and (3) a third step of introducing a second liquid into the solution introduction space, wherein the second liquid includes a second solvent immiscible with the first solvent, discharging, into the solution discharge space, the first liquid introduced into the solution introduction space, and thereby forming, within the cavities, a droplet of the first liquid coated with the second liquid and containing the microscopic body.

[2] The method according to the item [1], wherein, in the first step, the solution discharge space is provided above the bottom surface of the insertion member and between the substrate and the insertion member.

[3] The method according to the item [1], wherein, in the first step, the solution discharge space is provided above the bottom surface of the insertion member and within the substrate.

[4] The method according to the item [1], wherein, in the first step, the solution discharge spaces are provided above the bottom surface of the insertion member and between the substrate and the insertion member and within the substrate.

[5] The method according to the item [1], wherein, in the first step, the solution discharge space is provided above the bottom surface of the insertion member and within the insertion member.

[6] The method according to the item [1], wherein, in the first step, the solution discharge spaces are provided above the bottom surface of the insertion member and between the substrate and the insertion member and within the insertion member.

[7] The method according to any one of the items [1] to [6], wherein, in the second step, the first liquid is introduced into the solution introduction space via a flow passage formed in the insertion member and/or the substrate and having an outlet in the solution introduction space.

[8] The method according to the item [2], wherein
the insertion member has a bobbin-like shape including fringes at both ends in an insertion direction,
the bottom surface of the insertion member defines a first fringe having substantially the same shape as that of the cavity-formed surface of the substrate, and
the first fringe divides an upper space above the cavity-formed surface of the substrate into two spaces, the two spaces including the solution introduction space positioned between the bottom surface and the cavity-formed surface and the solution discharge space positioned above the first fringe.

[9] The method according to any one of the items [1] to [8], the method further including, between the second step and the third step, a step of controlling a temperature of the substrate in which the cavities are formed.

[10] A method of enclosing a microscopic body in at least some of a plurality of cavities formed in a surface of a substrate and separated from each other, the method including the steps of:
(A) arranging an insertion member above a cavity-formed surface of the substrate such that a bottom surface of the insertion member and the cavity-formed surface of the substrate face each other, and introducing a first liquid into a solution introduction space thus formed between the bottom surface of the insertion member and the cavity-formed surface of the substrate, wherein the first liquid includes the microscopic body and a first solvent;
(B) introducing a second liquid into the solution introduction space, wherein the second liquid includes a second solvent immiscible with the first solvent, discharging the first liquid introduced into the solution introduction space as a portion of the first liquid introduced into the solution introduction space and the cavities into a solution discharge space that is in communication with the solution introduction space, and thereby forming, within the cavities, a droplet of the first liquid coated with the second liquid and containing the microscopic body.

[11] A method of detecting a microscopic body enclosed in at least some of a plurality of cavities formed in a surface of a substrate and separated from each other, the method including:
(1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and providing a solvent discharge space that is in communication with the solution introduction space, the solvent discharge space being located above the bottom surface of the insertion member, and between the substrate and the insertion member, within the substrate and/or within the insertion member;
(2) a second step of introducing a first liquid into the solution introduction space, wherein the first liquid includes the microscopic body and a first solvent;
(3) a third step of introducing a second liquid into the solution introduction space, wherein the second liquid includes a second solvent immiscible with the first solvent, discharging, into the solvent discharge space, the first liquid introduced into the solution introduction space, and thereby forming, within the cavities, a droplet of the first liquid coated with the second liquid and containing the microscopic body; and
(4) a fourth step of optically, electrically and/or magnetically detecting the microscopic body present in the droplet.

[12] A method of optically detecting a microscopic body enclosed in at least some of a plurality of cavities formed in a surface of a substrate and separated from each other, wherein the microscopic body is optically detected on the basis of a change in absorbance and/or fluorescence of a chromogenic substrate, the method including:
(1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and providing a solvent discharge space that is in communication with the solution introduction space, the solvent discharge space being located above the bottom surface of the insertion member, and between the substrate and the insertion member, within the substrate and/or within the insertion member;
(2) a second step of introducing a first liquid including the microscopic body, the chromogenic substrate, and a first solvent into the solution introduction space;
(3) a third step of introducing a second liquid into the solution introduction space, wherein the second liquid includes a second solvent immiscible with the first solvent, discharging, into the solvent discharge space, the first liquid introduced into the solution introduction space, and thereby forming, within the cavities, a droplet of the first liquid coated with the second liquid and containing the microscopic body; and
(4) a fourth step of detecting a change in absorbance and/or fluorescence of the chromogenic substrate present in the droplet.

[13] A microscopic body detection device including a substrate including a surface having a plurality of cavities formed therein so as to be separated from each other such that microscopic bodies are enclosed in the cavity; and an insertion member arranged above a cavity-formed surface of the substrate, in which
the insertion member includes a support section for determining a relative position of the insertion member relative to the substrate;
a solution introduction space is provided, between the cavity-formed surface of the substrate and a bottom surface of the insertion member arranged above the cavity-formed surface to face the cavity-formed surface;

a solution discharge space is provided that is in communication with the solution introduction space, the solution discharge space being provided above the bottom surface of the insertion member, and between the substrate and the insertion member, within the substrate and/or within the insertion member; and a flow passage is formed in the insertion member and/or the substrate, the flow passage having an outlet in the solution introduction space.

[14] The device according to the item [13], wherein a first solvent held in the solution introduction space is substituted by a second solvent that is immiscible with the first solvent, the second solvent being introduced into the solution introduction space via the flow passage, and the substituted first solvent is allowed to be discharged to the solution discharge space.

[15] The device according to the item [14], wherein a first liquid held in the solution introduction space as a portion of the first liquid held in the solution introduction space and the cavity and including the microscopic body and the first solvent is discharged to the solution discharge space by a second liquid including the second solvent immiscible with the first solvent and being introduced into the solution introduction space via the flow passage, and a droplet of the first liquid coated with the second liquid and containing the microscopic body is formed in the cavity.

[16] The device according to the item [13], wherein the solvent discharge space is provided above the bottom surface of the insertion member and between the substrate and the insertion member.

[17] The device according to the item [13], wherein the solvent discharge space is provided above the bottom surface of the insertion member and within the substrate.

[18] The device according to the item [13], wherein the solvent discharge spaces are provided above the bottom surface of the insertion member and between the substrate and the insertion member and within the substrate.

[19] The device according to the item [13], wherein the solvent discharge space is provided above the bottom surface of the insertion member and within the insertion member.

[20] The device according to the item [13], wherein the solvent discharge spaces are provided above the bottom surface of the insertion member and between the substrate and the insertion member and within the insertion member.

[21] The device according to the item [13], wherein the insertion member has a bobbin-like shape including fringes at both ends in an insertion direction, the bottom surface of the insertion member defines a first fringe having substantially the same shape as that of the cavity-formed surface of the substrate, and the first fringe divides an upper space above the cavity-formed surface of the substrate into two spaces, the two spaces including the solution introduction space positioned between the first fringe and the cavity-formed surface and the solution discharge space positioned above the first fringe.

[22] The device according to the item [21], wherein the support section is a second fringe provided at a peripheral portion of an upper end of the insertion member, the second fringe is brought into locking engagement with the substrate when the insertion member is arranged above the cavity-formed surface of the substrate, and a height of the insertion member from the first fringe to the second fringe defines a height of the solution discharge space.

[23] The device according to the item [22], wherein a portion of the insertion member between the first fringe and the second fringe has a cylindrical shape, and the first fringe and the second fringe have a disc shape.

[24] The device according to any one of the items [21] to [23], wherein the first fringe has a property of not allowing light to pass therethrough.

[25] The device according to the item [21], wherein the support section is a projection provided on the bottom surface of the insertion member, and a height of the projection defines a height of the solution introduction space.

[26] The device according to any one of the items [21] to [25], wherein a gap created between the first fringe and the substrate brings the solution introduction space and the solution discharge space into communication with each other such that liquid is allowed to flow when the insertion member is arranged above the cavity-formed surface.

[27] The device according to any one of the items [21] to [25], wherein the first fringe of the insertion member includes a notch, and the notch brings the solution introduction space and the solution discharge space into communication with each other such that liquid is allowed to flow when the insertion member is arranged above the cavity-formed surface.

[28] The device according to any one of the items [13] to [27], wherein the insertion member has a property of not allowing light to pass therethrough at least at its bottom surface.

[29] The device according to any one of the items [13] to [26], wherein the support section is brought into fitting engagement with the substrate when the insertion member is arranged above the cavity-formed surface of the substrate.

[30] The device according to any one of the items [13] to [29], further including a temperature controller that controls a temperature of the substrate.

[31] The device according to any one of the items [13] to [30], further comprising a detector that optically, electrically, and/or magnetically detects the microscopic body present in the cavity.

[32] A method of enclosing a microscopic body in a cavity, the method including the following steps:

(1) a step of bringing an insertion member into detachable contact with s substrate, wherein the insertion member has a surface, the substrate has a surface in which a plurality of cavities are formed, when the insertion member is brought into detachable contact with the substrate, the surface of the insertion member is positioned above the surface of the substrate with a sufficiently small distance for inducing a capillary phenomenon, thereby a liquid introduction space is formed between the two surfaces, a plane that includes the surface of the insertion member defines a threshold level, and the liquid introduction space is in communication with a space above the threshold level at least via a first flow passage and a second flow passage;

(2) a step of introducing a first liquid into the liquid introduction space via the first flow passage, wherein the first liquid includes a first solvent and a target microscopic body; and (3) a step of introducing a second solvent via the first flow passage or the second flow passage into the liquid introduction space to replace the first liquid in the liquid introduction space by the second solvent, wherein the second solvent is immiscible with the first solvent.

Advantageous Effects of Invention

The present invention provides a technique for enclosing to-be-detected substances such as nucleic acids, proteins, viruses, cells, etc. in droplets of an extremely small volume by a simplified operation and enabling highly sensitive detection.

BRIEF DESCRIPTION OF DRAWINGS

FIG. 2-1 is a diagram explaining a step of a microscopic body detection method and a microscopic body enclosing method using the microscopic body detection device in accordance with the first embodiment.

FIG. 2-2 is a diagram explaining a step of the microscopic body detection method and the microscopic body enclosing method using the microscopic body detection device in accordance with the first embodiment.

FIG. 2-3 is a diagram explaining a step of the microscopic body detection method and the microscopic body enclosing method using the microscopic body detection device in accordance with the first embodiment.

FIG. 2-4 is a diagram explaining a step of the microscopic body detection method and the microscopic body enclosing method using the microscopic body detection device in accordance with the first embodiment.

FIG. 3 is a diagram for explanation of a reaction product resulting from the reaction between an enzyme present on a surface of a virus particle and a chromogenic substrate.

FIG. 4 is a diagram illustrating a modified example of the plug in accordance with the first embodiment.

DESCRIPTION OF EMBODIMENTS

Figure 1:
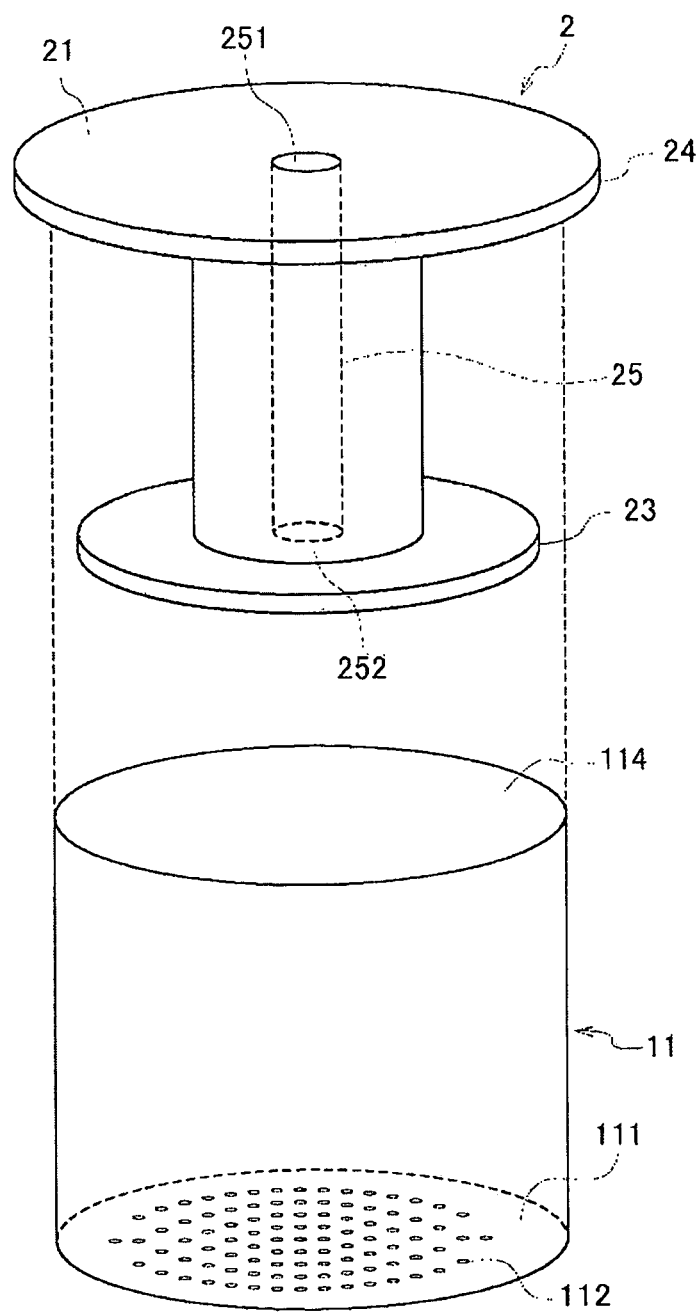
FIG. 1 is a diagram illustrating a well and a plug of a microscopic body detection device in accordance with a first embodiment of the present invention.

Preferable embodiments of the present invention will be described hereinbelow with reference to the drawings. It should be noted that the embodiments described hereinbelow depict an example of a representative embodiment of the present invention, by which the scope of the present invention is in no way interpreted in a limitative manner.

A substance enclosing method in accordance with the present invention is a method of enclosing a microscopic body in at least some of a plurality of cavities (which may be hereinafter referred to as "receptacle") formed in a surface of a substrate (which may be hereinafter referred to as "array"), where the cavities are separated from each other by a sidewall. The microscopic body enclosing method in accordance with the present invention includes the following steps (A), (B), and (C):

(A) a step of arranging an insertion member (which may be hereinafter referred to as "plug") above a receptacle-formed surface of the array, determining the relative positions of the plug and the array by a support section provided on the plug such that a bottom surface of the plug and the receptacle-formed surface of the array face each other, thereby providing a solution introduction space between the bottom surface of the plug and the receptacle-formed surface of the array, and providing a solution discharge space that is in communication with the solution introduction space, the solution discharge space being provided above the bottom surface of the plug, and between the array and the plug, within the array and/or within the plug (plug insertion step);

(B) a step of introducing a first liquid including the microscopic body and a first solvent into the solution introduction space (substance introduction step); and (C) a step of introducing a second liquid into the solution introduction space, wherein the second liquid includes a second solvent immiscible with the first solvent, discharging the first solvent in the solution introduction space into the solution discharge space, and thereby forming, within the receptacle, a droplet of the first liquid coated with the second liquid and containing the microscopic body (substance enclosing step).

Also, a microscopic body detection method in accordance with the present invention is a method of detecting a microscopic body enclosed in the above-described receptacle, which includes the following step (D) in addition to the above-described steps (A) to (C) of the microscopic body enclosing method:

(D) a step of optically, electrically and/or magnetically detecting the microscopic body present in the droplet (detection step).

The microscopic body detection method in accordance with the present invention will be described hereinbelow. A microscopic body enclosing method and a microscopic body detection device in accordance with the present invention will also be described in the course of the description and illustration of the microscopic body detection method.

[Substance to be Detected]

The microscopic body that should be detected by the microscopic body detection method or the like in accordance with the present invention (which may also be hereinafter referred to as a "target substance") is not limited to a particular one as long as the microscopic body is a substance with a size that allows the substance to be accommodated in the receptacle. Target substance may be a nucleic acid, a protein, a sugar, a lipid, and a complex thereof, as well as a virus, a cell, and a subcellular organelle. Also, the target substance may be resin or metal particles (beads) having the binding ability for binding to the above-mentioned substances. The target substance is preferably a nucleic acid, a protein, a sugar, a lipid, and a complex thereof, which can be a marker of various diseases or infectious diseases, as well as a cell and a subcellular organelle, or a carrier having the binding ability for binding thereto.

Nucleic acids include natural nucleic acids such as DNA and RNA, and artificial nucleic acids such as LNA and PNA, and also include polymers thereof. Also, cells include animal cells, plant cells, bacterial cells, and the like. Subcellular organelles include liposomes, exosomes, mitochondria, and the like.

Here, the term "bead," which is used synonymously with "particle," is a technical term commonly used in the technical field. Although the shape of the bead is not limited to a particular one, the shape of the bead is usually spherical. The material of the beads is not limited to any particular one, either, and may be glass, silicon, rubber, polystyrene, polypropylene, polyvinyl pyrrolidone, polyacrylamide, polystyrene dextran, cross-linked dextran (Sephadex™), agarose gel (Sepharose™), silica gel, latex gel, acrylic resin, copolymer of vinyl and acrylamide, cellulose, nitrocellulose, cellulose derivative, gelatin, magnetic material, and the like. The beads may be porous. The beads preferably have an average particle diameter of 5 μm or less, and for example, about 1 μm to 4 μm. It should be noted that the term "average particle diameter" refers to a numerical value measured using electron microscope observation or dynamic light scattering.

In order to give the beads the binding ability for binding to nucleic acids, proteins, sugars, lipids, and complexes thereof, as well as viruses, cells and subcellular organelles, etc., for example, the complementary strand to the nucleic acid may be immobilized on the beads, or an antibody against proteins and the like may be immobilized on the beads. The binding ability for binding to a target substance can be imparted to the beads by using known intermolecular binding reactions such as nucleic acid hybridization reaction and antigen-antibody reaction.

Immobilization of nucleic acid chains and antibodies on beads may be performed by traditionally known methods. For example, a complementary strand or an antibody may be bound to a modifying group on the surface of a bead via a linker. In the case of an amino-group-modified bead, a nucleic acid chain or an antibody can be covalently bonded to an amino group present on the surface through a cross-linking agent having N-hydroxysuccinimide or the like.

First Embodiment

[Array]

Figure 2:
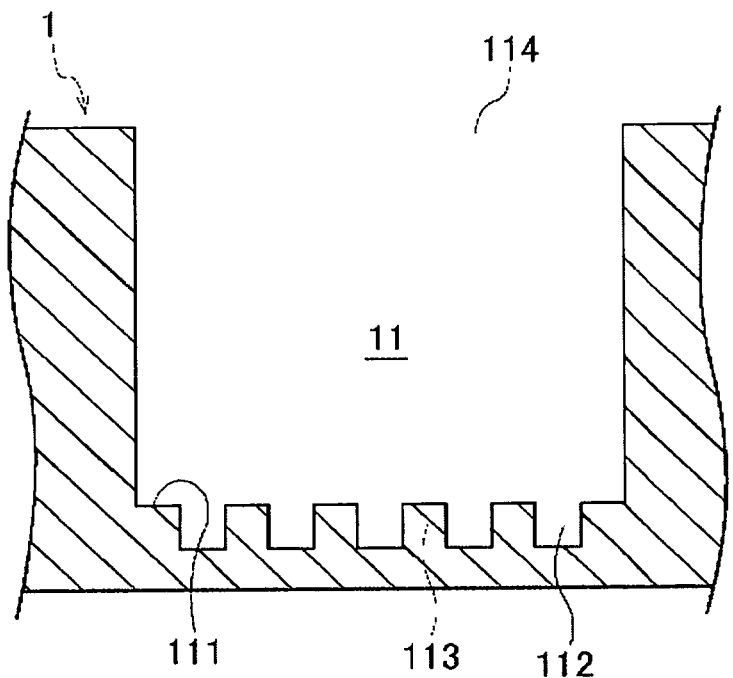
Figure 1:
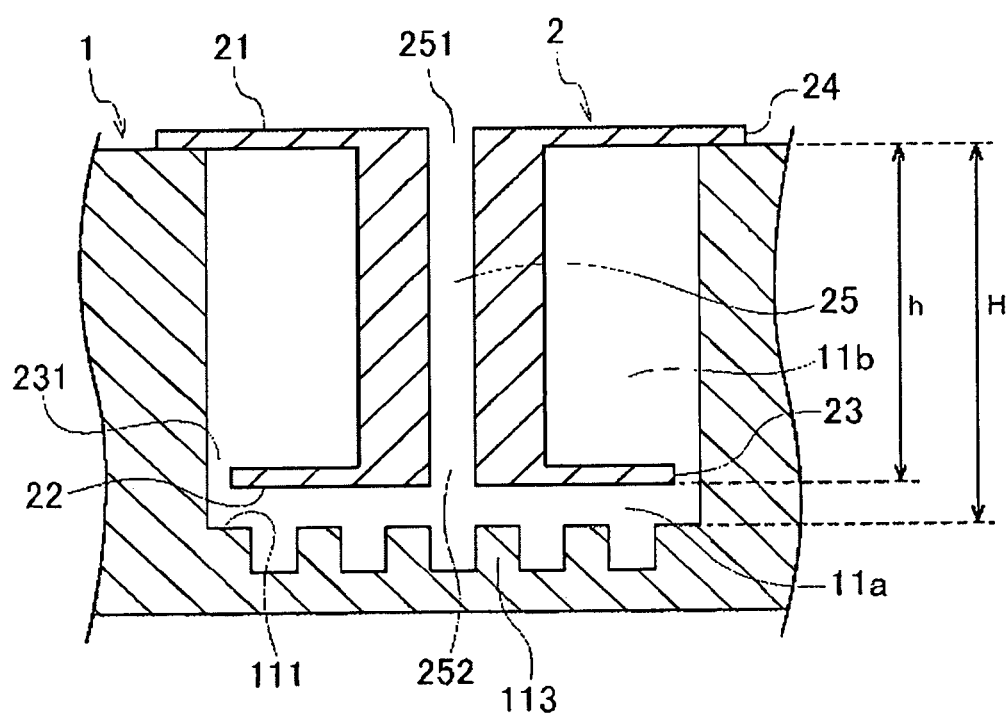
Figure 2:
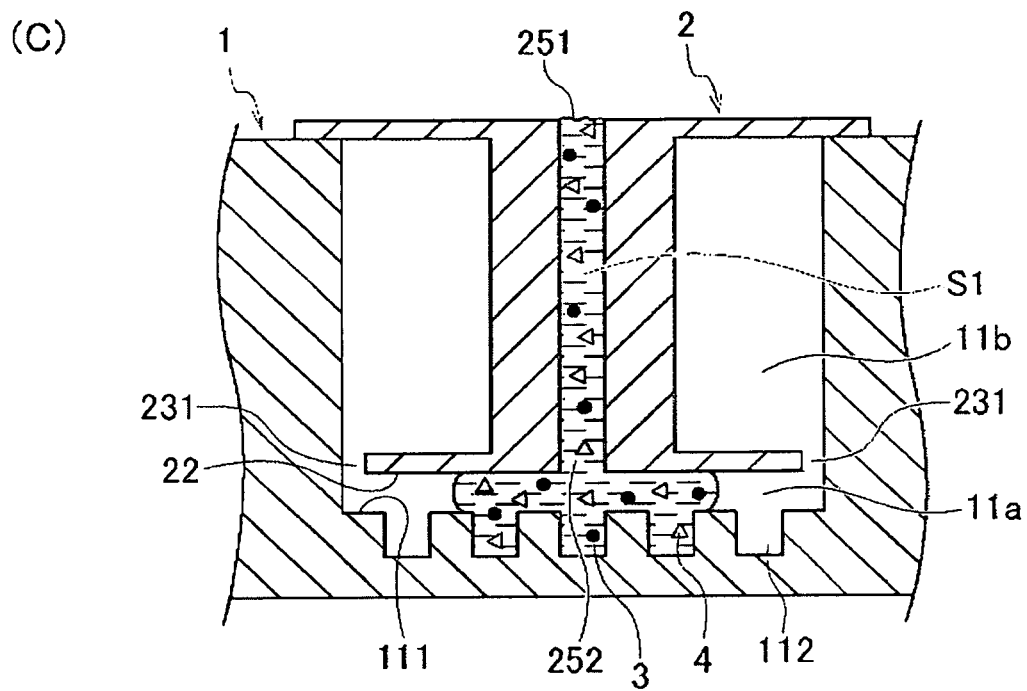
Figure 2:
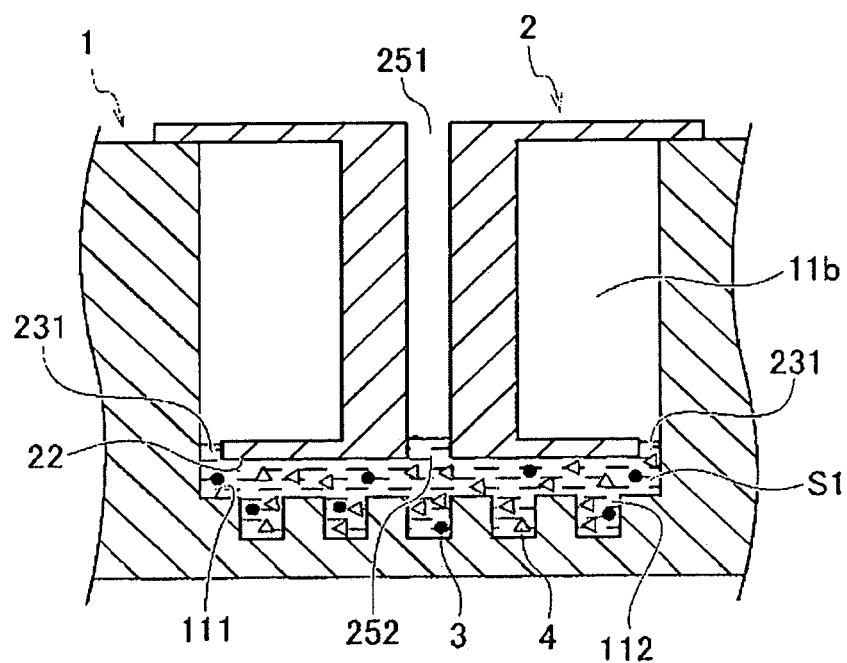
Figure 2:
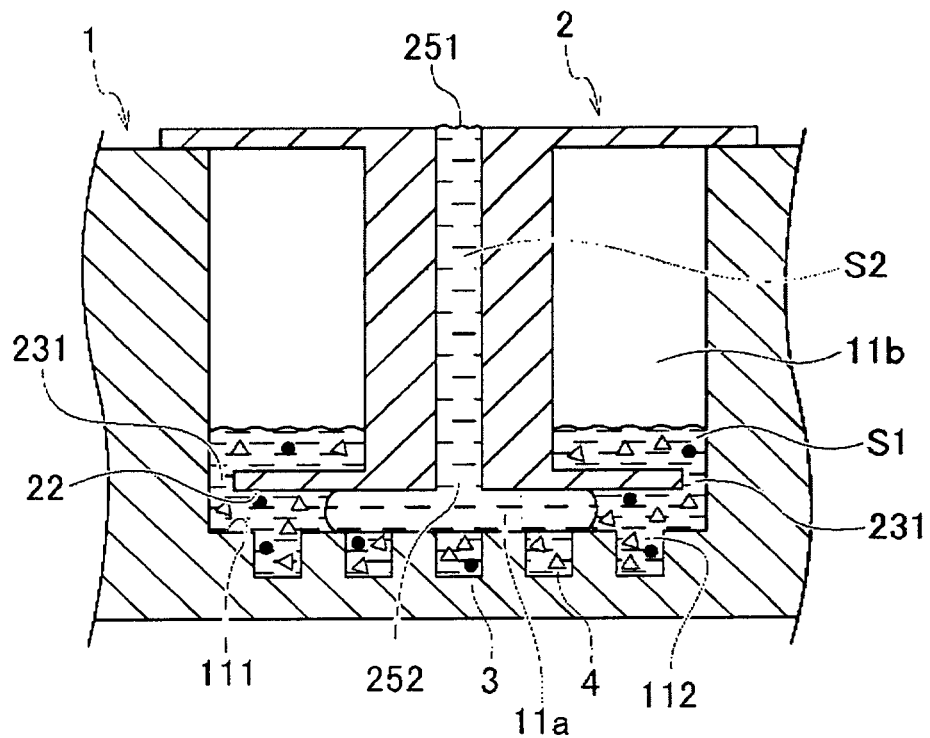

The device used in the microscopic body detection method in accordance with the present invention includes an array and a plug. FIGS. 1 and 2(A) illustrate the configurations of the array and the plug. A well 11 is formed in the array 1 (see FIG. 2(A)). A plurality of wells 11 may be formed in the array 1. A plurality of receptacles 112 for accommodating the target substances are formed in the bottom surface 111 of the well 11 (hereinafter, the bottom surface 111 is referred to as a "receptacle-formed surface 111"). The receptacles 112 are separated from one another by sidewalls 113.

The array 1 can be formed using known techniques such as wet etching or dry etching of a glass substrate layer, or nanoimprinting, injection molding, or cutting of a plastic substrate layer. The material of the array 1 is a material having optical transparency in the case of optical detection of a target substance, and may be glass or various plastics (PP, PC, PS, COC, COP, PDMS, etc.). For the array 1, it is preferable to select a material that has less autofluorescence and less wavelength dispersion and causes less optical errors.

The array 1 may be configured by a commercially available 96-well plate provided with 96 wells 11.

The size (volume) and shape of the well 11 are not subject to particular limitations as long as the plug 2 is allowed to be in fitting engagement therewith. The size of the well 11 may be about 5 to 10 mm, typically about 7 mm at its diameter on the receptacle-formed surface 111, and the depth (see the symbol H in FIG. 2(B)) is about 10 to 12 cm. The shape of the well 11 is preferably cylindrical or prismatic considering ease of formation of the well 11 and the plug 2.

While the number of receptacles 112 in each well 11 is not subject to particular limitations, the number of receptacles 112 is about 100,000 to 1,000,000, preferably about 200,000 to 500,000.

The size (volume) and shape of the receptacle 112 should be such that the receptacle 112 can accommodate the target substance. The size of the receptacle 112 may be about 4 to 8 μm in diameter at its bottom, which is typically about 5 μm, and about 6 to 12 μm in depth, where its volume is in the order of femtoliters.

The shape of the well 11 is also preferably cylindrical or prismatic considering ease of molding.

[Plug Insertion Step]

In this step, the plug 2 is arranged above the receptacle-formed surface 111 of the array 1, and the relative positions of the plug 2 and the array 1 with respect to each other is determined by the support section provided on the plug 2'. The bottom surface of the plug 2 and the receptacle-formed surface 111 of the array 1 are arranged to face each other, and thereby a solution introduction space is provided between the bottom surface of the plug 2 and the receptacle-formed surface 111 of the array 1. At the same time, a solution discharge space is provided above the bottom surface of the plug 2 and between the array 1 and the plug 2 such that the solution discharge space is in communication with the solution introduction space so that liquid is allowed to flow therein.

First, the plug 2 is inserted into the space of the well 11 via the opening 114 of the well 11 (see FIGS. 1 and 2(B)). Although a set of one well 11 and one plug 2 is depicted here, the array 1 may have a plurality of wells 11, in which case multiple plugs 2 by the number corresponding to the number of wells 11 should be used. The plug 2 may be removably inserted into the well 11.

The plug 2 has a bobbin-like shape with fringes at both ends in the insertion direction, and includes a first fringe 23 provided at a peripheral portion at a lower end in the insertion direction into the space of the well 11 and a bottom surface 22 facing the receptacle-formed surface 111 at the time of insertion into the space of the well 11 and having substantially the same shape as that of the receptacle-formed surface 111. Here, the bottom surface of the first fringe 23 and the bottom surface 22 constitute the same plane.

Also, the plug 2 includes a second fringe 24 provided at a peripheral portion of an upper end thereof in the insertion direction into the space of the well 11, where the second fringe 24 is provided as a support section that holds the bottom surface 22 at a position where the bottom surface 22 is kept out of contact with the well's bottom surface 111 when the plug 2 is inserted into the space of the well 11.

The above-mentioned "bobbin-like shape" means that the portion of the plug 2 between its first fringe 23 and second fringe 24 (which may be hereinafter referred to as a "main body of the plug 2") has a shape of a cylinder, and the first fringe 23 and the second fringe 24 are formed in disc shapes each extending from corresponding one of the both ends of the cylinder. The main body of the plug 2 may have a tapered shape, and preferably has a tapered shape whose diameter decreases toward the lower side in the insertion direction.

When the plug 2 is inserted into the space of the well 11, the second fringe 24 is preferably brought into fitting engagement with the array 1. As a result, by preventing the plug 2 once inserted from coming off again, erroneous operations can be eliminated, and it is made possible to prevent contamination due to the solution in the space of the well 11 spilling out due to the plug 2 being inadvertently removed.

The plug 2 includes a solvent introduction passage 25 having an inlet 251 in the top surface 21 and an outlet 252 in the bottom surface 22.

While the material of the plug 2 is not subject to particular limitations, the material of the plug 2 may be the same material as that of the array 1. The plug 2 can be shaped using known techniques such as plastic nanoimprinting, injection molding, cutting, etc., and can also be shaped using a 3D printer.

The first fringe 23 of the plug 2 has a smaller area than that of the receptacle-formed surface 111. That is, the projected area of the first fringe 23 in the insertion direction of the plug 2 into the space of the well 11 is smaller than the area of the receptacle-formed surface 111. Consequently, when the plug 2 is inserted into the space of the well 11, a gap 231 is formed between the first fringe 23 and the inner wall of the well 11.

The diameter of the well 11 is about 5 to 10 mm, typically about 7 mm, and the diameter (diameter of the bottom surface 22) of the first fringe 23 of the plug 2 is smaller than the diameter of the well 11 so as to form the gap 231 and, for example, it is reduced by about 5 to 30%.

When the plug 2 is inserted into the space of the well 11, the first fringe 23 divides the space of the well 11 into a solution introduction space 11a located between the receptacle-formed surface 111 and the first fringe 23 and a solution discharge space 11b located between the first fringe 23 and the second fringe 24. The solution introduction space 11a and the solution discharge space 11b are in fluid communication with each other by the gap 231 created between the first fringe 23 and the inner wall of the well 11.

Here, the bottom surface 22 of the plug 2 defines a "threshold level" in the sense that the solution introduction space 11a located below the bottom surface 22 of the plug 2 and the solution discharge space 11b located above the bottom surface 22 of the plug 2 are demarcated by the bottom surface 22 of the plug 2.

The second fringe 24 is brought into locking engagement with the edge of the opening of the well 11 when the plug 2 is inserted into the space of the well 11, and holds the bottom surface 22 in a position where the bottom surface 22 is kept out of contact with the receptacle-formed surface 111. For this purpose, the height h from the bottom surface 22 to the second fringe 24 of the plug 2 (i.e., the height of the solution discharge space 11b) is smaller than the depth H of the well 11.

[Substance Introduction Step]

Next, the first solution S1 including the target substance 3 and the first solvent is introduced into the solution introduction space 11a (see FIG. 2(C)).

Here, an example will be described in which a chromogenic substrate 4 for optically detecting the target substance 3 based on the change in absorbance and/or the fluorescence is introduced together with the target substance 3.

The first solvent may be any solvent suitable for dissolving or suspending the target substance 3 and the chromogenic substrate 4, and a solvent that is usually used when detecting nucleic acids, proteins, sugars, lipids, and complexes thereof, as well as viruses, cells, subcellular organelles, etc. is used as the first solvent. The first solution S1 may contain, for example, at least one selected, from the group consisting of water, alcohol, ether, ketone, nitrile solvent, dimethyl sulfoxide (DMSO), and N,N-dimethylformamide (DMF), or a mixture including the selected one, among which water is preferable. Examples of the alcohol may include ethanol, methanol, propanol, glycerin, and the like. Examples of the ether may include tetrahydrofuran, polyethylene oxide, 1,4-dioxane, and the like. Examples of the ketone may include acetone, methyl ethyl ketone, and the like. Examples of the nitrile solvent may include acetonitrile and the like.

The first solvent may contain a buffer substance. While the buffer substance is not limited to a particular one, so-called Good's Buffers such as MES (2-morpholinoethanesulfonic acid), ADA (N-(2-acetamido) iminodiacetic acid), PIPES (piperazine-1,4-bis (2-ethanesulfonic acid)), ACES (N-(2-Acetamido)-2-aminoethanesulfonic acid), BES (N,N-Bis(2-hydroxyethyl)-2-aminoethanesulfonic acid), TES (N-Tris(hydroxymethyl)methyl-2-aminoethanesulfonic acid), HEPES (4-(2-hydroxyethyl)-1-piperazineethanesulfonic acid); Tris (Tris(hydroxymethyl)aminomethane); DEA (Diethanolamine); and the like may be used according to the pKa of the fluorescent dye.

Also, the first solvent may contain a surfactant. When the first solvent contains the surfactant, the first solution S1 can be more easily introduced into the solution introduction space 11a and the receptacle 112. While the surfactant is not subject to particular limitations, for example, TWEEN 20 (CAS number: 9005-64-5, polyoxyethylene sorbitan monolaurate) and Triton X-100 (CAS number: 9002-93-1 with the generic name of polyethylene glycol mono-4-octylphenyl ether (where n≈10)) may be mentioned. The concentration of the surfactant added to the first solvent is not subject to particular limitations but is preferably 0.01 to 1%.

Further, as the surfactant, anionic surfactants, cationic surfactants, nonionic surfactants, amphoteric surfactants, surfactants of natural origin, and the like can be widely used.

Anionic surfactants are classified into, for example, a carboxylic acid type, a sulfuric acid ester type, a sulfonic acid type, and a phosphoric acid ester type. Among these types, specifically, for example, sodium dodecyl sulfate, sodium laurate, sodium α-sulfofatty acid methyl ester, sodium dodecyl benzene sulfonate, sodium dodecyl ethoxylate sulfate, and the like may be mentioned, amongst which sodium dodecyl benzene sulfonate is preferably used.

Cationic surfactants are classified into, for example, a quaternary ammonium salt type, an alkylamine type, and a heterocyclic amine type. Specifically, for example, stearyl trimethyl ammonium chloride, distearyl dimethyl ammonium chloride, didecyl dimethyl ammonium chloride, cetyl tripyridinium chloride, dodecyl dimethyl benzyl ammonium chloride, and the like may be mentioned.

As the nonionic surfactant, for example, polyoxyethylene alkyl ether, polyoxyethylene hydrogenated castor oil, polyoxyethylene mono-fatty acid ester, polyoxyethylene sorbitan mono-fatty acid ester, sucrose fatty acid ester, polyglycerin fatty acid ester, alkyl polyglycoside, N-methyl alkyl glucamide, and the like may be mentioned. Amongst others, in addition to dodecyl alcohol ethoxylate, nonylphenol ethoxylate, lauroyl diethanolamide, those sold with the names of Triton X (such as Triton X-100), Pluronic (registered trademark) (such as Pluronic F-123, F-68), Tween (such as Tween 20, 40, 60, 65, 80, 85), Brij (registered trademark) (such as Brij 35, 58, 98), Span (Span 20, 40, 60, 80, 83, 85) will be preferable.

As the amphoteric surfactants, for example, lauryl dimethylaminoacetic acid betaine, dodecylaminomethyldimethylsulfopropylbetaine, 3-(tetradecyldimethylaminio)propane-1-sulfonate, are available, but it is preferable to use 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), or the like.

As a surfactant of natural origin, for example, lecithin and saponin are preferable, and among compounds referred to as lecithin, specifically, phosphatidylcholine, phosphatidylethanolamine, phosphatidylinositol, phosphatidylserine, phosphatidic acid, phosphatidylglycerol, and the like are preferable. Also, quillaja saponin is preferable as the saponin.

The first solution S1 including the target substance 3 and the chromogenic substrate 4 is injected via the inlet 251 of the solvent introduction passage 25 of the plug 2, and introduced via the outlet 252 into the solution introduction space 11a.

The amount of the first solution S1 introduced can be appropriately specified according to the volume of the solution introduction space 11a and is, for example, about 1 to 50 µl and preferably about 5 to 20 µl.

The diameter and shape of the solvent introduction passage 25 are not subject to particular limitations. For example, the shape may be a cylinder, an inner diameter of which is about 1 to 5 mm, typically about 2.5 mm.

The first solution S1 introduced into the solution introduction space 11a flows in the space between the bottom surface 111 of the well and the bottom surface 22 of the plug 2 through capillary action, and the solution introduction space 11a is filled with the first solution S1 (see FIG. 2(D)). Thus, the target substance 3 and the chromogenic substrate 4 are also introduced into the receptacle 112.

If the concentration of the target substance 3 in the first solution S1 is low, one molecule of the target substance 3 is introduced into the receptacle 112 or not introduced at all. The chromogenic substrate 4 is preferably contained in the first solution S1 at a sufficiently high concentration as compared to the concentration of the target substance 3. Accordingly, one molecule or two or more molecules of the chromogenic substrate 4 will be introduced into almost all of the receptacles 112.

[Substance Enclosing Step]

In this step, a second solution S2 that contains a second solvent that is immiscible with the first solution S1 is introduced into the solution introduction space 11a (see FIG. 2(E)). As a result, the first solution S1 in the solution introduction space 11a is forced to be discharged into the solution discharge space 11b and a droplet of the first solution S1 is formed within the receptacle 112. The droplet of the first solution S1 is coated with the second solution S2 and contains the target substance 3 and the chromogenic substrate 4.

The second solvent should be immiscible with the first solution S1. For example, at least one selected from the group consisting of saturated hydrocarbon, unsaturated hydrocarbon, aromatic hydrocarbon, silicone oil, hexafluoropropylene epoxide based polymer, polymer having a hydrofluoroether structure, perfluoropolyethers, trifluorochlorinated ethylene polymers, and polymers having a perfluorocarbon structure, or a mixture including the same or the like can be suitably used. Examples of saturated hydrocarbons include alkanes and cycloalkanes. Examples of alkanes include decane and hexadecane. Examples of unsaturated hydrocarbons include squalene and the like. As an aromatic hydrocarbon, benzene, toluene, and the like may be mentioned. Examples of hexafluoropropylene epoxide-based polymers include Krytox 143 (manufactured by DuPont), Krytox GPL (manufactured by DuPont), and the like. Examples of the polymer having a hydrofluoroether structure may include Asahi Clean AE 3000 (manufactured by Asahi Glass Co., Ltd.) and Novec 7000 (manufactured by Sumitomo 3M), and the like. Examples of the polymer having a perfluorocarbon structure include Fluorinert FC-40, Fluorinert FC-43 (manufactured by Sumitomo 3M): and the like.

Preferably, the second solvent to be used should have a higher specific gravity than that of the first solvent or the first solution S1 that includes the first solvent.

The second solution S2 is injected via the inlet 251 of the solvent introduction passage 25 of the plug 2 and introduced via the outlet 252 into the solution introduction space 11a.

While the amount of the second solution S2 introduced may be appropriately specified according to the volume of the solution introduction space 11a, the amount of introduction is about 1.1 to 5 times, preferably about 1.5 to 2 times the amount of introduction of the first solution S1.

The second solution S2 introduced into the solution introduction space 11a flows in the space between the receptacle-formed surface 111 and the bottom surface 22 of the plug 2 through capillary action. At this time, the first solution S1 with which the solution introduction space 11a is filled is forced to flow into the solution discharge space 11b through the gap 231, and is substituted by the second solution S2. As a result, a droplet D of the first solution S1 including the chromogenic substrate 4 coated with the second solution S2 is created in the receptacle 112 (see FIG. 2(F)). The target substance 3 is enclosed along with the chromogenic substrate 4 in a certain proportion of the droplets D created in the receptacle 112.

The solution discharge space 11b should have a volume that is sufficient for receiving the first solution S1 held in the solution introduction space 11a as portion of the first solution S1 held in the solution introduction space 11a and the receptacle 112. The volume of the solution discharge space 11b can be specified as appropriate according to the volume of the solution introduction space 11a, the number and volume of the receptacles 112, and the amount of introduction of the first solution S1.

In the next detection step, the target substance 3 present in the droplet D is detected optically, electrically, and/or magnetically. In the example described herein, the target substance 3 is optically detected through detection of the change in absorbance and/or fluorescence of the chromogenic substrate 4. More specifically, the explanation will be provided based, by way of example, on a case where the target substance 3 is a virus having on its surface or in its inside an enzyme having substrate cleaving activity vis-a-vis the chromogenic substrate 4 and the chromogenic substrate 4 is a substance which is cleaved by the enzyme to release a reaction product as a chromophore. However, while the chromogenic substrate 4 should be able to create a reaction product having optical characteristics after the reaction different from those before the reaction with the enzyme, the chromogenic substrate 4 may be a substance whose absorbance or optical rotation changes before and after the reaction, or a substance that exhibits fluorescence after the reaction.

Examples of combinations of such a virus and such an enzyme may be as follows.

TABLE 1

| | |
|---|---|
| Coronavirus | Hemagglutinin esterase |
| SARS virus | Hemagglutinin esterase |
| MARS virus | Hemagglutinin esterase |
| Influenza virus | Neuraminidase |
| Mumps virus (epidemic parotiditis) | Neuraminidase |
| Measles virus | Neuraminidase |
| Nipah virus | Neuraminidase |
| Canine distemper virus | Neuraminidase |

Figure 3:
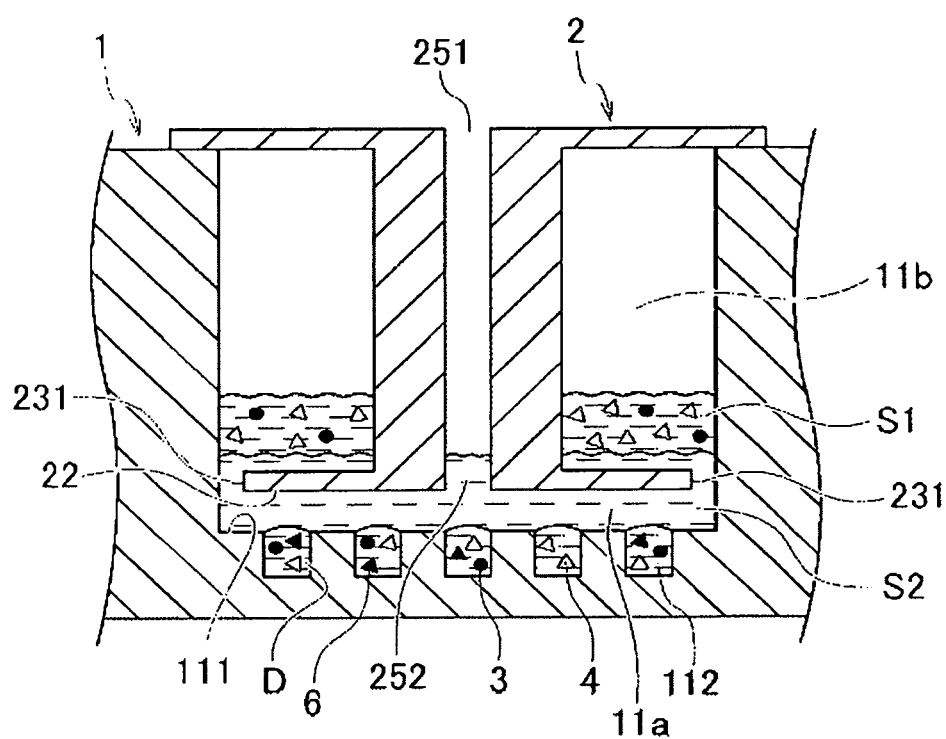

In the droplet D created in the receptacle 112, the reaction proceeds between the enzyme present on the surface of or in the inside of the target substance 3 (virus particle) and the chromogenic substrate 4, which coexist in the minimal volume, as a result of which a reaction product is created. This will be described in detail with reference to FIG. 3. The enzyme 31 is present on the surface of or in the inside of the virus particle (in the illustrated case, the enzyme 31 is present on the virus surface). When the chromogenic substrate 4 contacts and reacts with the enzyme 31, a reaction product 6 is created. The chromogenic product 6 exhibits optical characteristics different than those of the chromogenic substrate 4, and exhibits a shift in the absorbance or optical rotation or exhibits fluorescence (or luminescence).

The reaction product 6 is created and accumulated in the minimal volume of the droplet D by the reaction of the enzyme 31 and the chromogenic substrate 4. As a result, the creation of the reaction product 6 rapidly proceeds to a concentration detectable in the next detection step, so that it is made possible to implement highly sensitive detection of the reaction product 6.

More specific explanations will be provided, by way of example, based on a case where the virus is an influenza virus (see Table 1) and 4-methylumbelliferyl-α-D-neuraminic acid (4-methylumbelliferyl-N-acetyl-α-D-neuraminic acid: 4MU-NANA) is used as the chromogenic substrate 4.

Neuraminidase (enzyme 31) is present on the particle surface of the influenza virus. When the 4MU-NANA (chromogenic substrate 4) contacts and reacts with the neuraminidase, 4-methyl umbelliferone (reaction product 6) is created as a chromophore which exhibits fluorescence derived from hydrolysis of the 4MU-NANA by the neuraminidase. The 4-methyl umbelliferone is accumulated in the minimal volume of the droplet D, and the accumulated 4-methyl umbelliferone exhibits enhanced fluorescence.

While the reaction product 6 may be a product that can be created when the chromogenic substrate 4 and the enzyme 31 contact each other in the first solution S1 prior to this step, the created reaction product 6 is not accumulated in the minimal volume before the droplet D of the first solution S1 including the target substance 3 and the chromogenic substrate 4 is created in this step. As a result, for this reason, in the detection of the reaction product 6, the influence of the reaction product 6 created prior to this step is negligibly small.

[Detection Step]

In this step, the target substance 3 present in the droplet D is detected optically, electrically, and/or magnetically (see FIG. 2(G)). In the specific example described herein, the influenza virus as the target substance 3 is detected by detecting the fluorescence exhibited by the reaction product 6 (4-methylumbelliferone) created in the droplet D.

Optical detection can be carried out by a detector 7 that includes a light source, an optical path for collecting light from the light source in the inside of the receptacle 112 and collecting the resulting light from the inside of the receptacle 112 onto a sensor, and the sensor. The microscopic body detection device in accordance with the present invention may include the detector 7 in addition to the array 1 and the plug 2. The light emitted from the light source travels via the lower side of the array 1 (opposite to the opening surface of the well 11) into the receptacle 112, and the resulting light from the inside of the receptacle 112 is also collected via the same side. Lenses, filters, etc. used usually are arranged between the light source and the array 1 and between the array 1 and the sensor such as a CMOS image sensor.

Also, the microscopic body detection device in accordance with the present invention may include a temperature controller that controls the temperature of the array 1. The heating mechanism or temperature control mechanism disclosed in Patent Literature 2 can be adopted as the temperature controller. The temperature controller may be a heat block capable of temperature control, for example, by a Peltier element, a Joule-Thomson element, or the like.

As described above, although the reaction product 6 can be created in the first solution S1 even before the substance enclosing step, many of the reaction products 6 generated before the substance enclosing step are discharged from the solution introduction space 11a to the solution discharge space 11b by the second solution S2 in the substance enclosing step. For this reason, in the detection of the reaction product 6 from the lower side of the array 1 in this step, the reaction product 6 created before the substance enclosing step does not act as noise, and the signal from the reaction product 6 created and accumulated in the minimal volume of the droplet D can be selectively detected. In order to avoid detection of noise from the reaction product 6 discharged to the solution discharge space 11b, it is preferable that the first fringe 23 of the plug 2 does not allow light to pass therethrough. The property of not allowing transmission of light can be imparted thereto by forming the first fringe 23 or the entire plug 2 including the first fringe 23 with an opaque material.

The fluorescence of the 4-methyl umbelliferone (reaction product 6) in the droplet D is detected, and the enzyme activity of the neuraminidase is calculated using the acquired fluorescence intensity and a standard curve defining the relationship between the fluorescence intensity and neuraminidase activity prepared in advance. Further, determination of the presence or absence of the influenza virus or quantification of the number of particles is carried out using the calculated enzyme activity and a standard curve defining the relationship between the enzyme activity and the number of virus particles prepared in advance. Thus, the influenza virus as target substance 3 can be detected and the amount of viruses can also be determined quantitatively.

As described above, when the target substance 3 is diluted to a sufficiently low concentration in the first solution S1, the number of target substances 3 entering one receptacle 112 may be 0 or at most 1. In the substance enclosing step, the reaction product 6 can be accumulated at a high concentration in the droplet D of the first solution S1. As a result, even when only one particle of virus as the target substance 3 is in the receptacle 112, the reaction product 6 can be detected with high sensitivity. Accordingly, according to the substance detection method in accordance with the present invention, even a very small amount of the target substance 3 such as a virus can be detected with high sensitivity, and the amount thereof can be determined with high precision.

Also, in this process, the concentration of the target substance 3 can also be determined using the ratio of the number of the receptacles 112 in which the target substance 3 is detected to the number of the receptacles 112 in which the target substance 3 is not detected, and on the basis of a standard curve that defines the relationship between the concentration of target substance 3 in first solution S1 and the ratio prepared in advance.

According to this embodiment, it is possible to achieve a large-area array 1 having a large number of wells 11 and receptacles 112. For example, even in case of an array 1 having about one million receptacles 112, the target substance 3 can be efficiently enclosed in each of the receptacles 112 by a simplified operation. The time required from the substance introduction step to the substance enclosing step is very short, typically about 1 minute to 10 minutes, and the operation is simple.

According to the embodiment, since the target substance 3 can be detected with high sensitivity, it is made possible to detect the target substance 3 with a very low concentration in the order of 10 aM, which can be applied, for example, to applications such as Digital ELISA, ELISA-PCR, etc.

Modified Example of the First Embodiment

Figures 2, 3, 4:
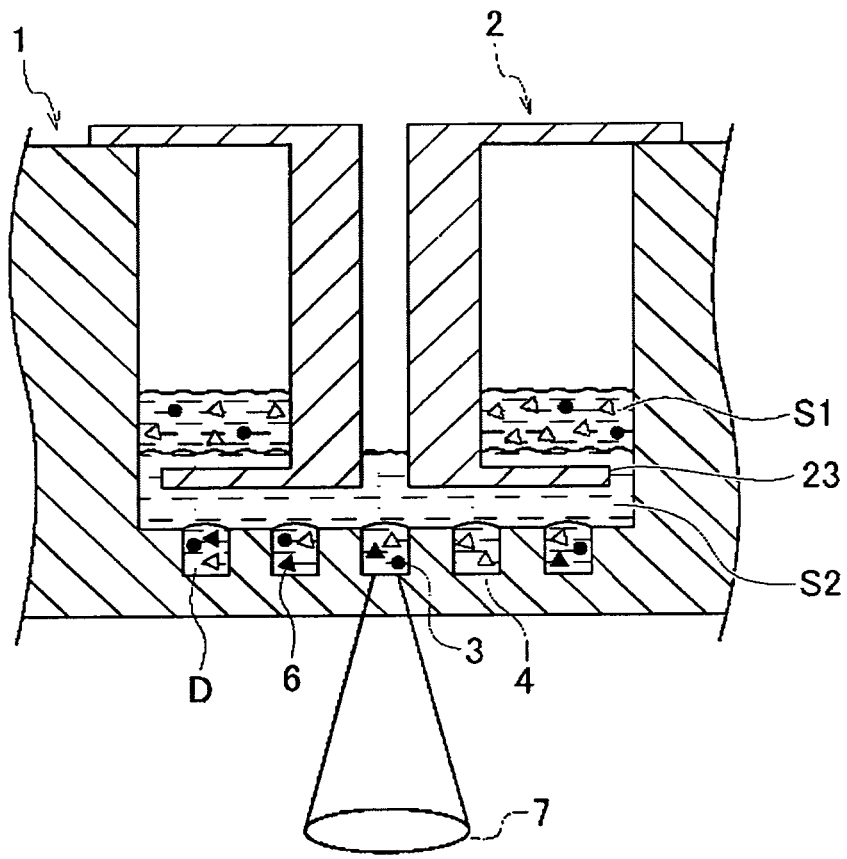
Figure 3:
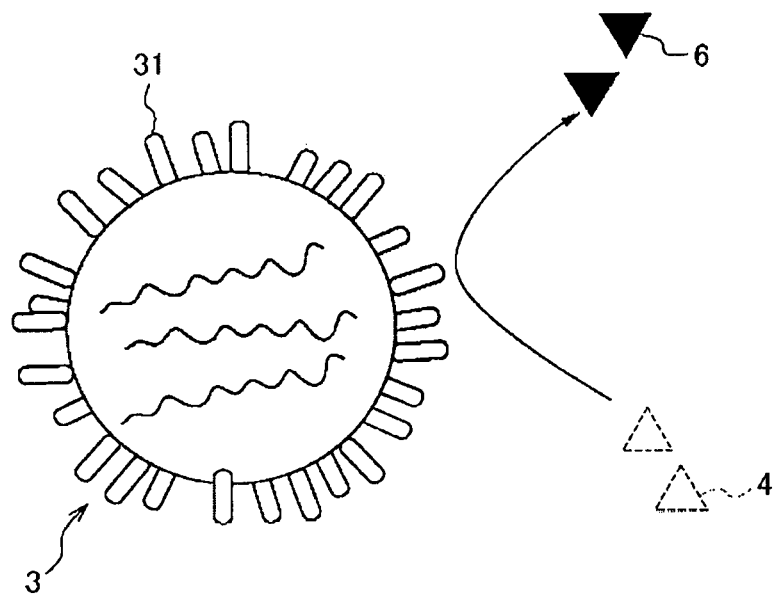
Figure 4:
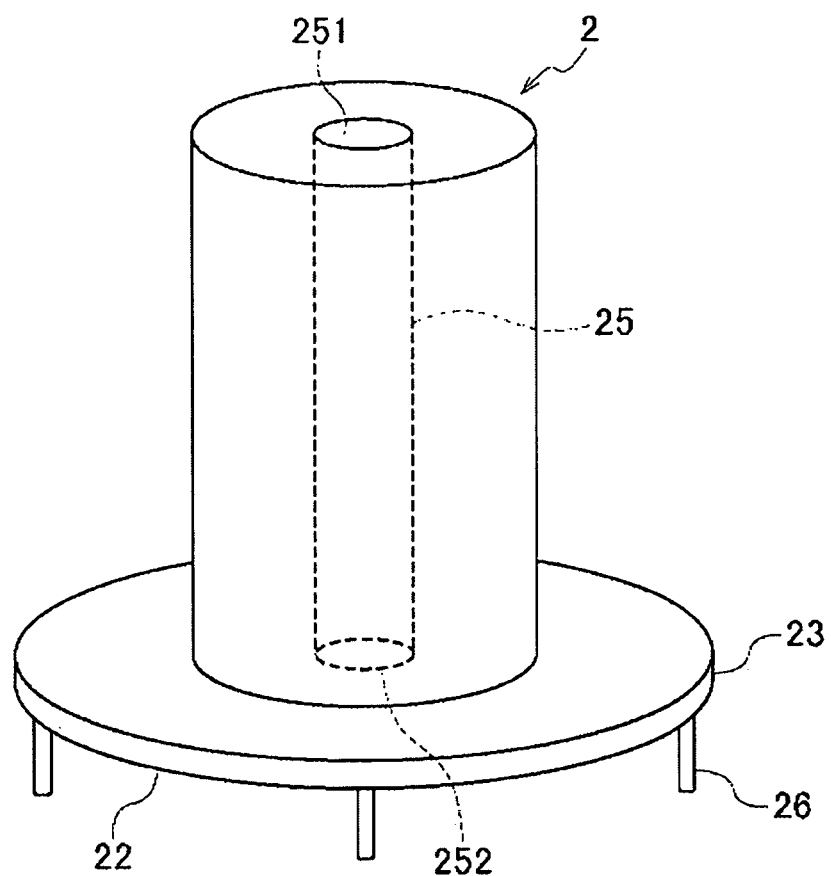
Figure 5:
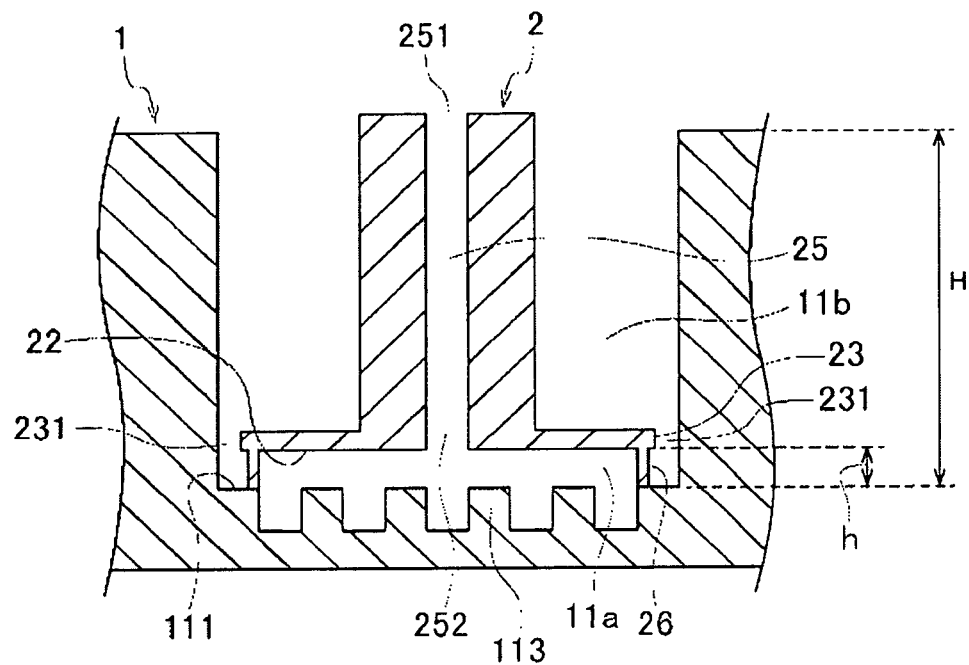
FIG. 5 is a diagram illustrating (A) the modified example of the plug illustrated in FIG. 4 and (B) another modified example of the plug in accordance with the first embodiment.
Figure 5:
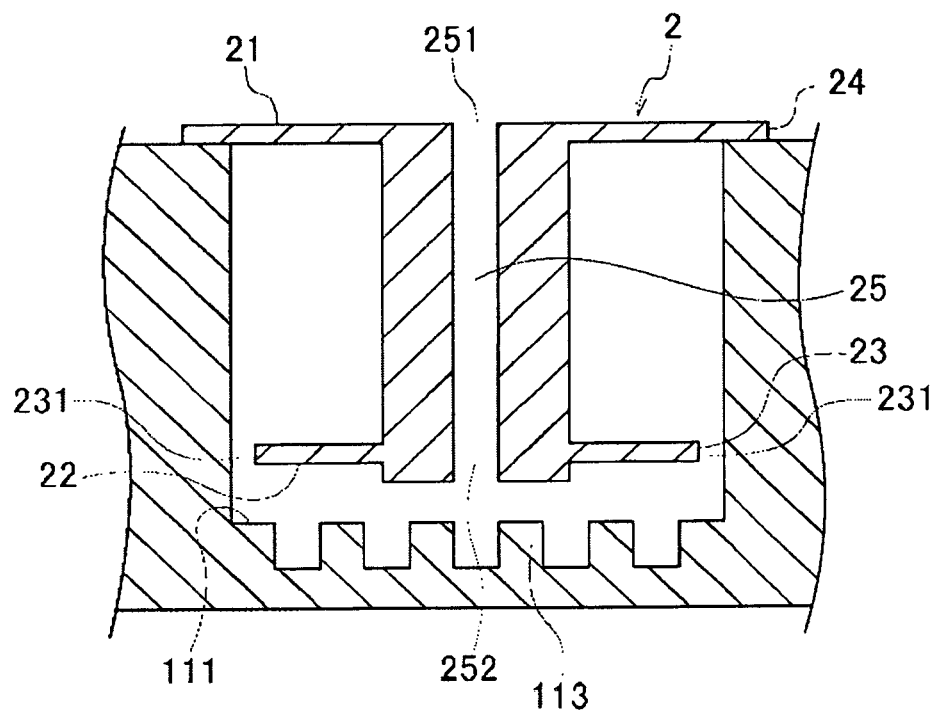

In the first embodiment described above, an example has been described in which the second fringe 24 functions as a support section that holds the bottom surface 22 such that it is kept out of contact with the receptacle-formed surface 111 when the plug 2 is inserted into the space of the well 11 (see FIGS. 1 and 2(A)). In the present invention, the support section of the plug 2 may be a projection 26 provided on the bottom surface 22 as illustrated in FIGS. 4 and 5(A). The height h of the projection 26 (i.e., the height of the solution introduction space 11a) is made smaller than the depth H of the well 11. The number of the projections 26 is not limited to a particular number but is preferably about 3 to 4 in order to realize stable positioning.

Also, in the first embodiment described above, an example has been described in which the bottom surface 22 of the plug 2 constitutes the same plane with the bottom surface of the first fringe 23 (see FIGS. 1 and 2(A)). In the present invention, however, as illustrated in FIG. 5(B), it suffices that the first fringe 23 be provided near the lower end in the insertion direction of the plug 2, so that the first fringe 23 does not need to be located at the lower end.

Figure 6:
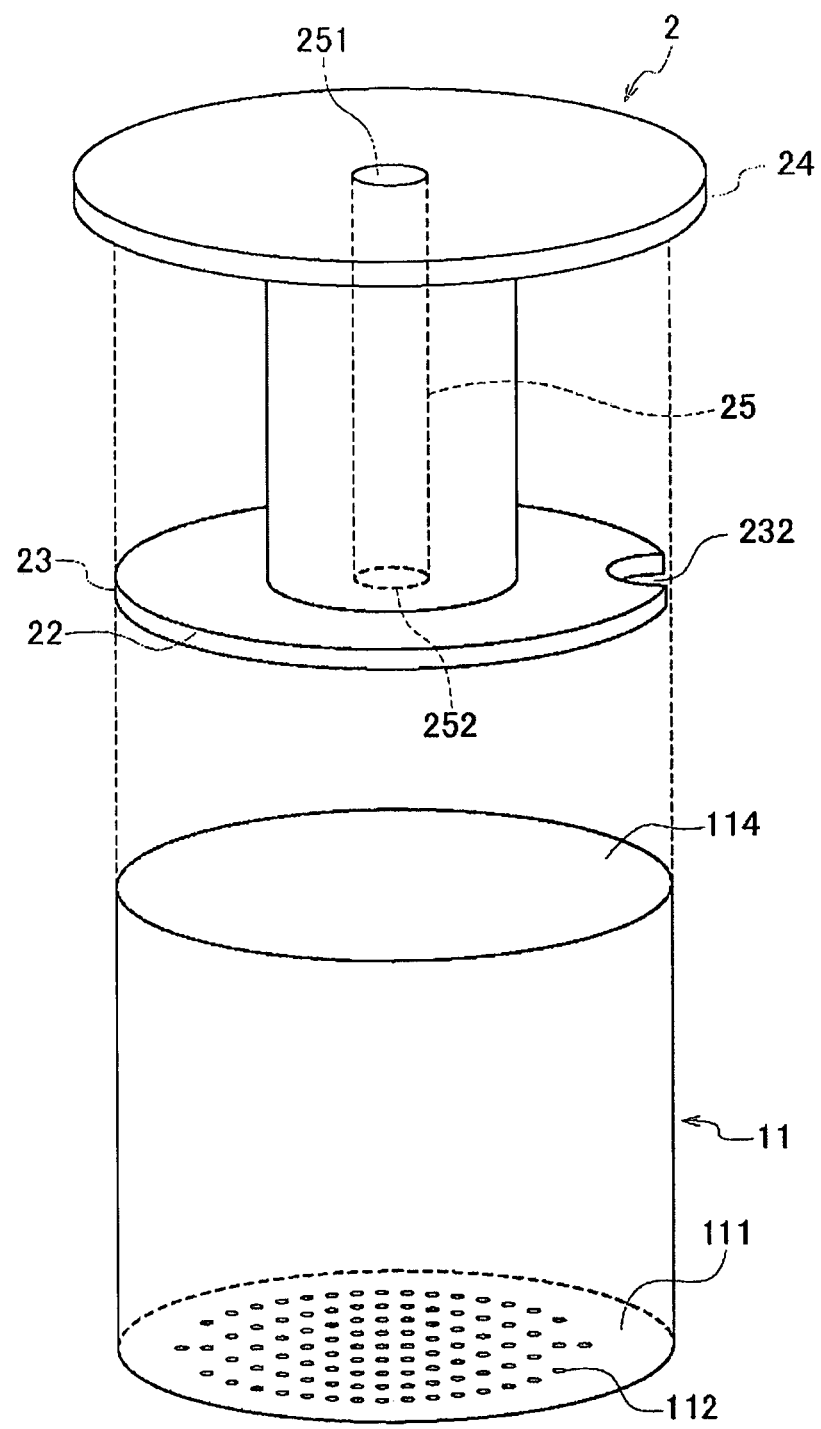
FIG. 6 is a diagram illustrating another modified example of the plug in accordance with the first embodiment.
Figure 7:
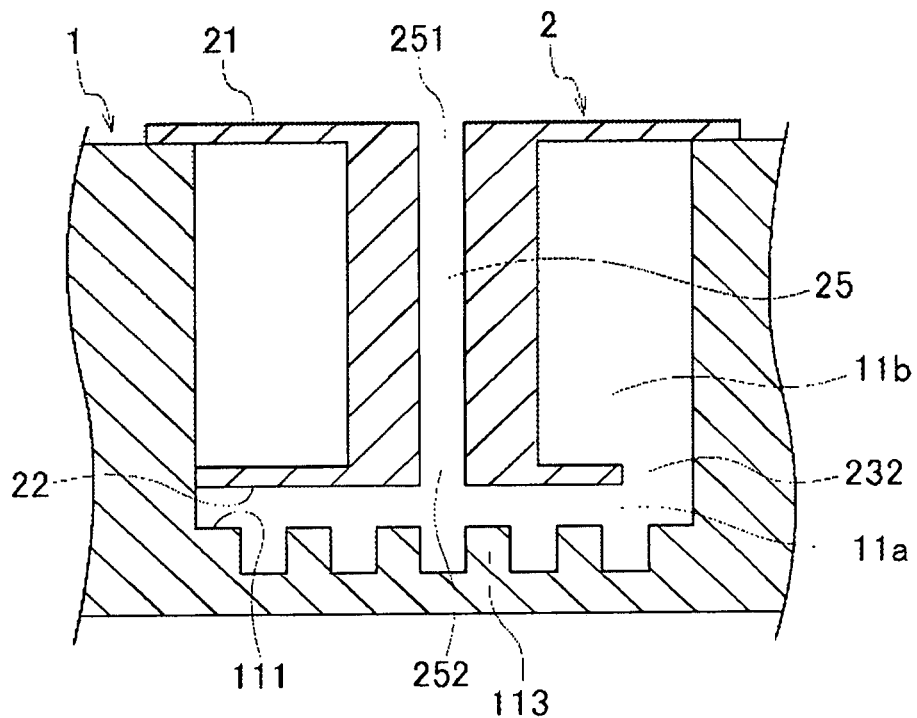
FIG. 7 is a diagram illustrating a configuration of the modified example of the plug illustrated in FIG. 6.

Further, in the first embodiment described above, an example has been described in which the solution introduction space 11a and the solution discharge space 11b of the well 11 are in communication via the gap 231 created between the first fringe 23 and the inner wall of the well 11 so that liquid is allowed to flow therein. In the present invention, however, the solution introduction space 11a and the solution discharge space 11b may be configured to be in communication by means of a notch 232 provided in the first fringe 23 of the plug 2 so that liquid is allowed to flow therein as illustrated in FIGS. 6 and 7. In this case, the first fringe 23 of the plug 2 does not need to have a smaller area than that of the receptacle-formed surface 111. Although the size and number of notch 232 are not subject to particular limitations, it is preferable that the notches 232 be provided with a sufficient size and by a sufficient number such that the first solution S1 forced to flow out by the second solution S2, which has been introduced into the solution introduction space 11a in the substance enclosing step, is allowed to promptly move to the solution discharge space 11b via the notch 232.

Figure 8:
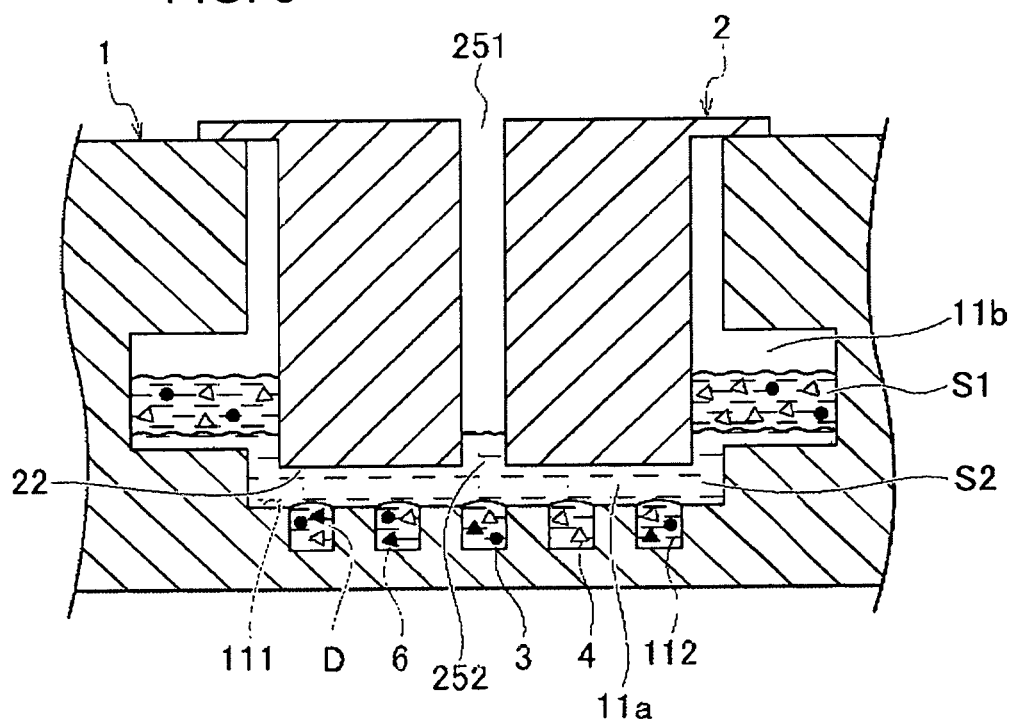
FIG. 8 is a diagram illustrating another modified example of an array and the plug in accordance with the first embodiment of the present invention.

In addition, in the above-described first embodiment, an example has been described in which, in the substance enclosing step, the first solution S1 is discharged into the solution discharge space 11b which is positioned between the plug 2 and the array 1 (specifically, the region defined by (a) the first fringe 23, the second fringe 24, and the main body of the plug 2 with the bobbin-like shape and (b) the surface of the well 11 facing the main body of the plug 2). In the present invention, however, the plug 2 may be configured to not include the first fringe 23 (see FIG. 8). In this case as well, the solution introduction space 11a is formed between the receptacle-formed surface 111 of the array 1 and the bottom surface 22 of the plug 2 facing the receptacle-formed surface 111. In addition, in this case, the solution discharge space 11b for discharging the first solution S1 introduced into the solution introduction space 11a can be formed by recessing the surface of the well 11 which faces the main body of the plug 2 and positioned above the bottom surface 22 of the plug 2. The bottom surface 22 of the plug 2 defines a "threshold level" in the sense that the solution introduction space 11a located below the bottom surface 22 of the plug 2 and the solution discharge space 11b located above the bottom surface 22 of the plug 2 are demarcated by the bottom surface 22 of the plug 2.

In the context of the present invention, the term "solution discharge portion 11b provided in the array 1" also encompasses a solution discharge portion 11b which is provided by partially recessing the surface of the well 11 facing the main body of the plug 2 in this manner.

Figure 9:
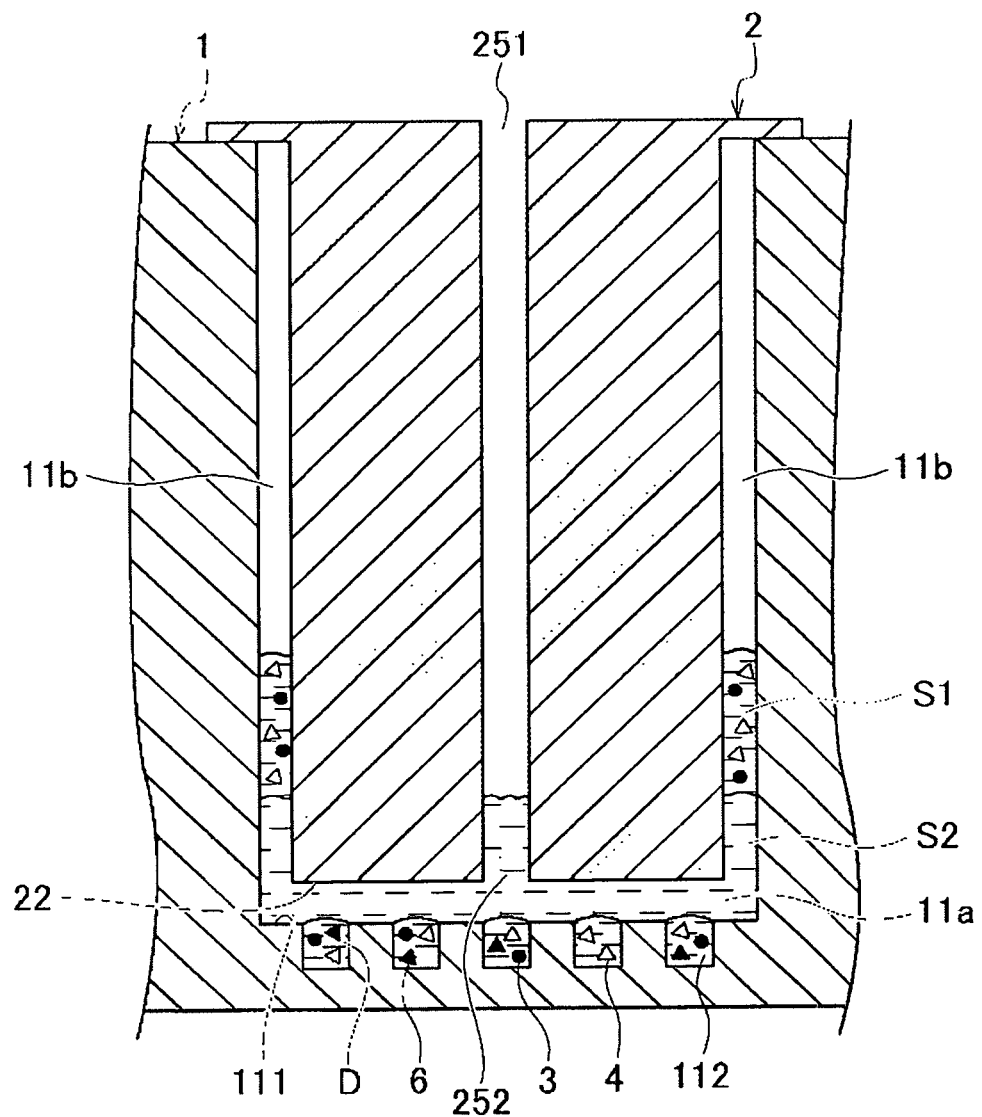
FIG. 9 is a diagram illustrating another modified example of the array and the plug in accordance with the first embodiment of the present invention.

It should be noted that, even when the plug 2 is configured to not include the first fringe 23, the solution discharge space 11b can be provided between the plug 2 and the array 1 without recessing the surface of the array 1 facing the plug 2 (see FIG. 9).

Second Embodiment

In the first embodiment described above, an example has been described in which the solution discharge space 11b is provided between the plug 2 and the array 1 (specifically, the region including and being defined by the main body of the plug 2 and the surface of the well 11 facing the main body of the plug 2). In the present invention, however, the "solution discharge portion 11b provided in the array 1" may be provided in a region of the array 1 independent of the surface thereof facing the plug 2. Meanwhile, in this case as well, the solution discharge space 11b needs to be in communication with the solution introduction space 11a so that liquid is allowed to flow therein.

A microscopic body enclosing method using the microscopic body detection device in accordance with the second embodiment will be described hereinbelow with reference to FIG. 10.

[Plug Insertion Step]

In this step, the plug 2 is arranged above the receptacle-formed surface 111 of the array 1, and the relative positions of the plug 2 and the array 1 with respect to each other is determined by the second fringe 24 provided on the plug 2 such that the bottom surface 22 of the plug 2 and the receptacle-formed surface 111 of the array 1 are arranged to face each other, and thereby a solution introduction space 11a is provided between the bottom surface 22 of the plug 2 and the receptacle-formed surface 111 of the array 1. At the same time, a solution discharge space 11b is provided above the bottom surface 22 of the plug 2, and within the array 1 such that the solution discharge space 11b is in communication with the solution introduction space 11a so that liquid is allowed to flow therein.

First, the plug 2 is inserted into the space of the well 11 via the opening 114 of the well 11 of the array 1 in the same manner as in the first embodiment.

Figure 10A:
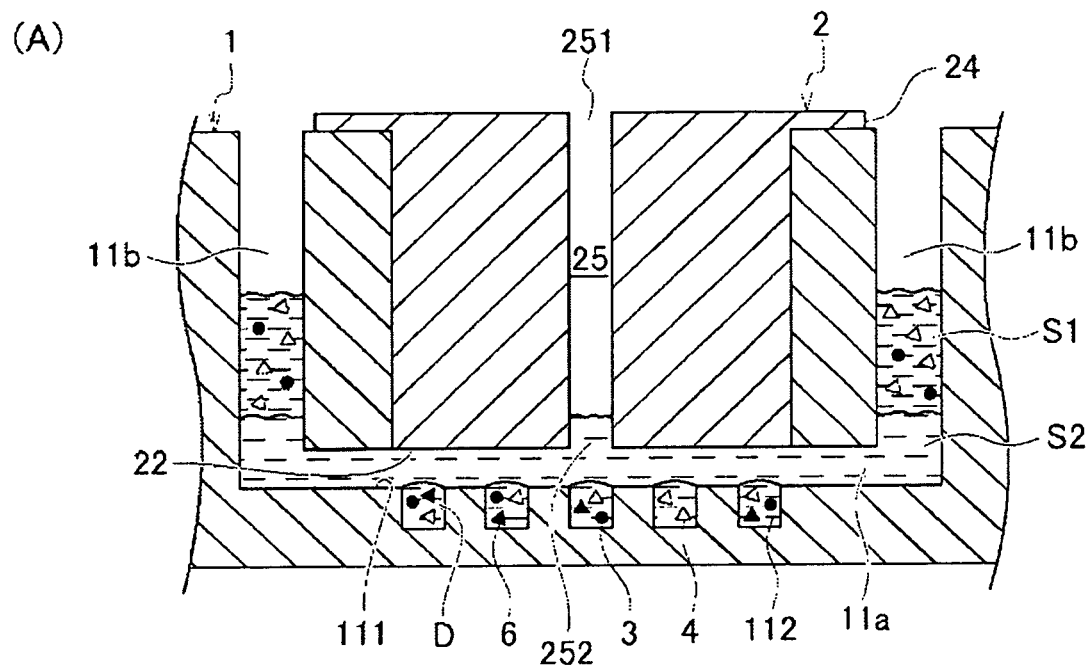
FIG. 10 is a diagram illustrating another modified example of the array and the plug in accordance with a second embodiment of the present invention.
Figure 10B:
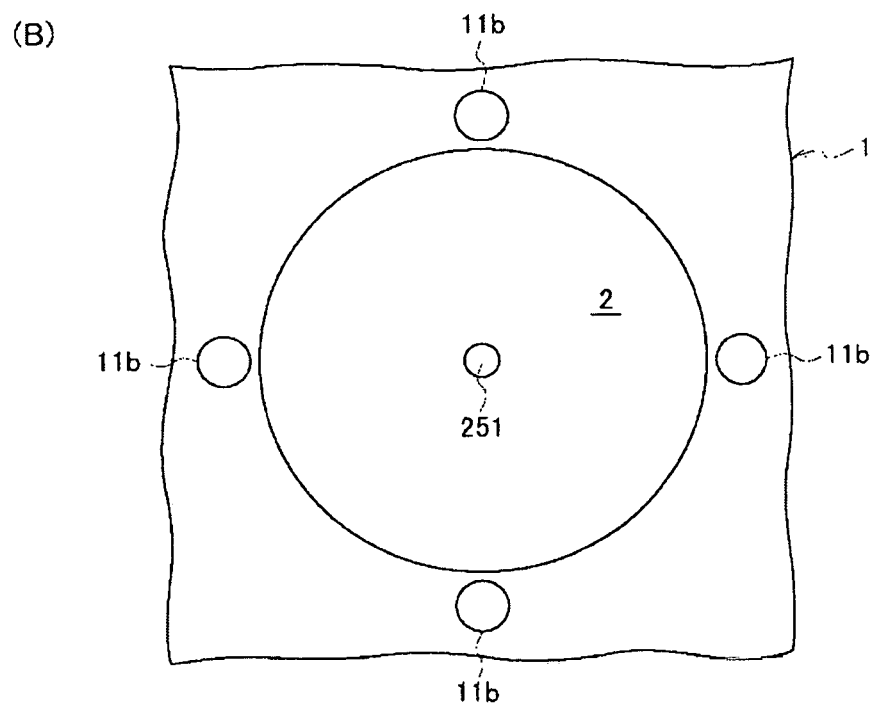

The plug 2 illustrated in FIG. 10 adopts a configuration that does not include the first fringe 23. The second fringe 24 is brought into locking engagement with the edge of the opening of the well 11 when the plug 2 is inserted into the space of the well 11, and holds the bottom surface 22 in a position where the bottom surface 22 is kept out of contact with the receptacle-formed surface 111. Also, when the plug 2 is inserted into the space of the well 11, the bottom surface 22 of the plug 2 faces the receptacle-formed surface 111 such that a solution introduction space 11a is created between the bottom surface 22 and the receptacle-formed surface 111.

When the plug 2 is inserted into the space of the well 11, the second fringe 24 is preferably brought into fitting engagement with the array 1. As a result, by preventing the plug 2 once inserted from coming off again, erroneous operations can be eliminated, and it is made possible to prevent contamination due to the solution in the space of the well 11 spilling out due to the plug 2 being inadvertently removed.

[Substance Introduction Step]

Next, the first solution S1 including the target substance 3 and the first solvent is introduced into the solution introduction space 11a.

The first solution S1 including the target substance 3 and the chromogenic substrate 4 is injected via the inlet 251 of the solvent introduction passage 25 of the plug 2, and introduced via the outlet 252 into the solution introduction space 11a. The first solution S1 introduced into the solution introduction space 11a flows in the space between the receptacle-formed surface 111 and the bottom surface 22 of the plug 2 through capillary action, and the solution introduction space 11a is filled with the first solution S1. Thus, the target substance 3 and the chromogenic substrate 4 are also introduced into the receptacle 112. Preferably, one target substance 3 is introduced into one receptacle 112 on a one-to-one basis.

[Substance Enclosing step]

After the cooling step is performed as needed in the same manner as in the first embodiment, a second solution S2 that contains a second solvent that is immiscible with the first solution S1 is introduced into the solution introduction space 11a.

The array 1 in accordance with this embodiment includes a region that is in communication with the solution introduction space 11a below the bottom surface 22 of the plug 2 and the lower portion of this region that is below the bottom surface 22 of the plug 2 is integral with the solution introduction space 11a. The region is extended upward of the array 1 and the upper portion of the region that is above the bottom surface 22 of the plug 2 functions as the solution discharge space 11b. The bottom surface 22 of the plug 2 defines a "threshold level" in the sense that the solution introduction space 11a located below the bottom surface 22 of the plug 2 and the solution discharge space 11b located above the bottom surface 22 of the plug 2 are demarcated by the bottom surface 22 of the plug 2.

It should be noted that, while a case is illustrated in FIG. 10 where four solution discharge spaces 11b are provided in the array 1, the number of the solution discharge spaces 11b is not limited to any particular number.

The second solution S2 is injected via the inlet 251 of the solvent introduction passage 25 of the plug 2 and introduced via the outlet 252 into the solution introduction space 11a. The second solution S2 introduced into the solution introduction space 11a flows in the space between the receptacle-formed surface 111 and the bottom surface 22 of the plug 2 through capillary action. At this time, the first solution S1 with which the solution introduction space 11a is filled is forced to flow out to the solution discharge space 11b and substituted by the second solution S2. As a result, droplets D of the first solution S1 including the chromogenic substrate 4 coated with the second solution S2 are formed in the receptacle 112 (see FIG. 10).

Modified Example of the Second Embodiment

Figure 11:
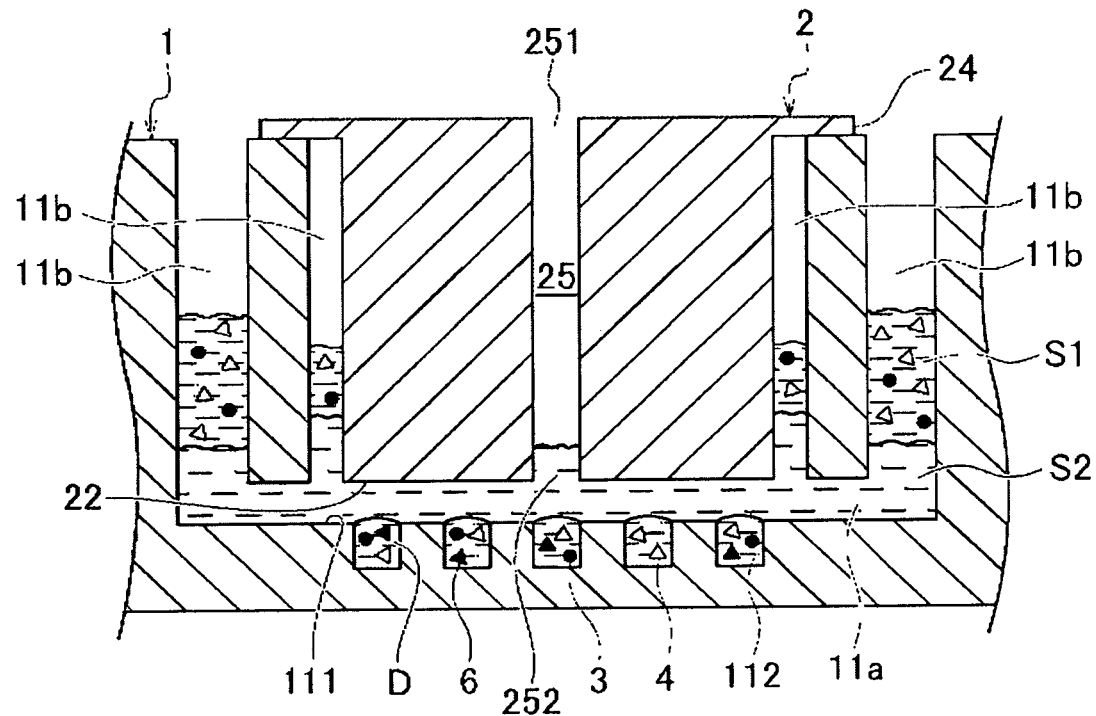
FIG. 11 is a diagram illustrating another modified example of the array and the plug in accordance with the second embodiment.

In the above-described second embodiment, the solution discharge space 11b may be provided not only in the array 1 but also between the plug 2 and the array 1 (see FIG. 11).

Third Embodiment

Further, in the present invention, the solvent discharge space 11b may be provided within the plug 2. In this case, the solution discharge space 11b is configured to be brought into communication with the solution introduction space 11a such that liquid is allowed to flow therein when the plug 2 is inserted into the space of the well 11.

A microscopic body enclosing method using the microscopic body detection device in accordance with the third embodiment will be described hereinbelow with reference to FIG. 12.

[Plug Insertion Step]

In this step, the plug 2 is arranged above the receptacle-formed surface 111 of the array 1, and the relative positions of the plug 2 and the array 1 with respect to each other are determined by the projection 26 provided on the plug 2 such that the bottom surface 22 of the plug 2 and the receptacle-formed surface 111 of the array 1 are arranged to face each other, and thereby a solution introduction space 11a is provided between the bottom surface 22 of the plug 2 and the receptacle-formed surface 111 of the array 1. At the same time, a solution discharge space 11b is provided above the bottom surface 22 of the plug 2 and within the plug 2 such that the solution discharge space 11b is in communication with the solution introduction space 11a so that liquid is allowed to flow therein.

First, the plug 2 is inserted into the space of the well 11 via the opening 114 of the well 11 of the array 1 in the same manner as in the first embodiment.

Figure 12:
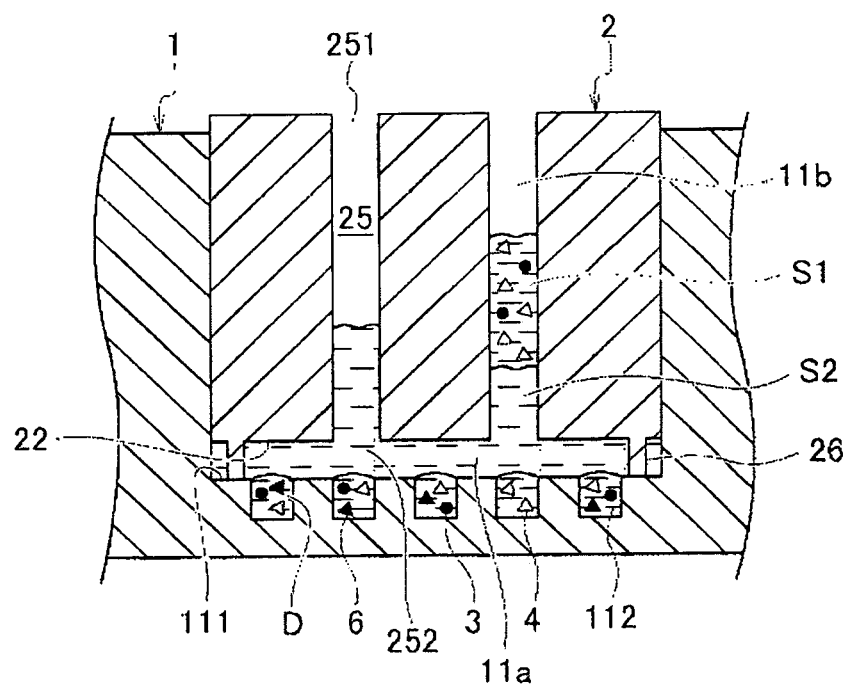
FIG. 12 is a diagram illustrating another modified example of the array and the plug in accordance with a third embodiment of the present invention.

The plug 2 illustrated in FIG. 12 adopts a configuration that doe's not include the first fringe 23. Also, the plug 2 includes a projection 26 provided on the bottom surface 22 as a support section that holds the bottom surface 22 at a position where the bottom surface 22 is kept out of contact with the receptacle-formed surface 111 when the plug 2 is inserted into the space of the well 11. When the plug 2 is inserted into the space of the well 11, the bottom surface 22 of the plug 2 faces the receptacle-formed surface 111 such that a solution introduction space 11a is created between the bottom surface 22 and the receptacle-formed surface 111.

When the plug 2 is inserted into the space of the well 11, the second fringe 24 is preferably brought into fitting engagement with the substrate 1. As a result, by preventing the plug 2 once inserted from coming off again, erroneous operations can be eliminated, and it is made possible to prevent contamination due to the solution in the space of the well 11 spilling out due to the plug 2 being inadvertently removed.

[Substance Introduction Step]

Next, the first solution S1 including the target substance 3 and the first solvent is introduced into the solution introduction space 11a.

The first solution S1 including the target substance 3 and the chromogenic substrate 4 is injected via the inlet 251 of the solvent introduction passage 25 of the plug 2, and introduced via the outlet 252 into the solution introduction space 11a. The first solution S1 introduced into the solution introduction space 11a flows in the space between the receptacle-formed surface 111 and the bottom surface 22 of the plug 2 through capillary action, and the solution introduction space 11a is filled with the first solution S1. Thus, the target substance 3 and the chromogenic substrate 4 are also introduced into the receptacle 112.

[Substance Enclosing step]

After the cooling step is performed as needed in the same manner as in the first embodiment, a second solution S2 that contains a second solvent that is immiscible with the first solution S1 is introduced into the solution introduction space 11a.

The plug 2 in accordance with this embodiment includes a region that is brought into communication with the solution introduction space 11a when the plug 2 is inserted into the space of the well 11, and the upper portion of this region that is above the bottom surface 22 of the plug 2 functions as the solution discharge space 11b. The bottom surface 22 of the plug 2 defines a "threshold level" in the sense that the solution introduction space 11a located below the bottom surface 22 of the plug 2 and the solution discharge space 11b located above the bottom surface 22 of the plug 2 are demarcated by the bottom surface 22 of the plug 2.

It should be noted that the number of the solution discharge spaces 11b provided in the plug 2 is not limited to a particular number.

The second solution S2 is injected via the inlet 251 of the solvent introduction passage 25 of the plug 2 and introduced via the outlet 252 into the solution introduction space 11a. The second solution S2 introduced into the solution introduction space 11a flows in the space between the receptacle-formed surface 111 and the bottom surface 22 of the plug 2 through capillary action. At this time, the first solution S1 with which the solution introduction space 11a is filled is forced to flow out to the solution discharge space 11b and the first solution S1 in the solution introduction space 11a is substituted by the second solution S2. As a result, droplets D of the first solution S1 including the chromogenic sub-strate 4 coated with the second solution S2 are formed in the receptacles 112 (see FIG. 12).

Modified Example of the Third Embodiment

Figure 13:
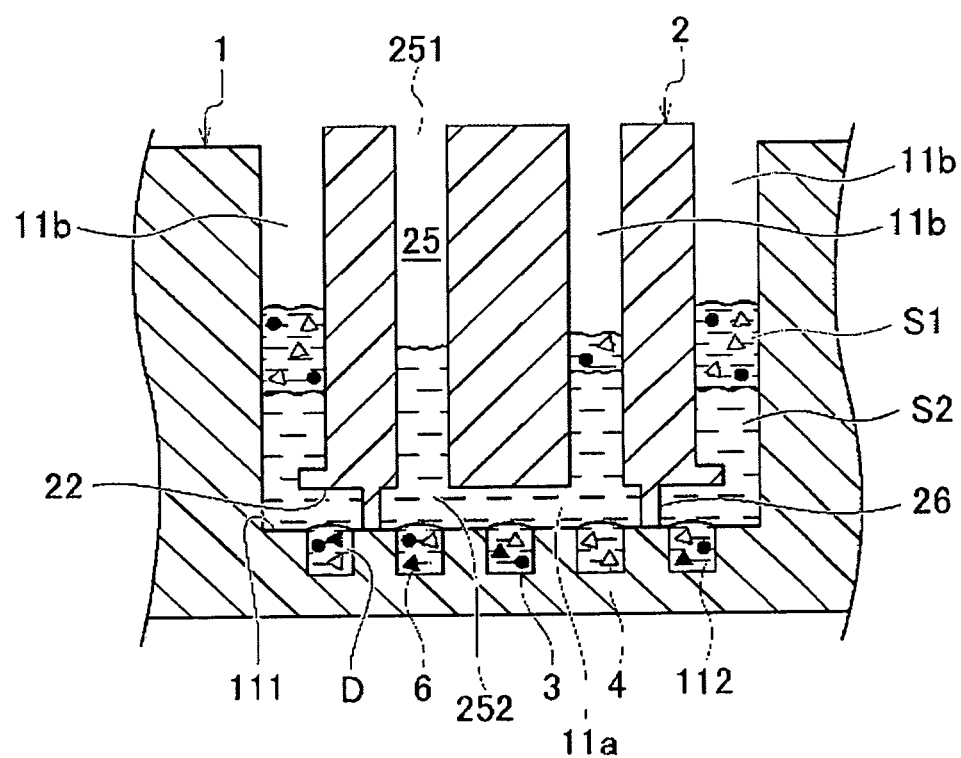
FIG. 13 is a diagram illustrating another modified example of the array and the plug in accordance with the third embodiment.

In the above-described third embodiment, the solution discharge space 11b may be provided not only in the plug 2 but also between the plug 2 and the array 1 (see FIG. 13).

EXAMPLES

Figure 14A:
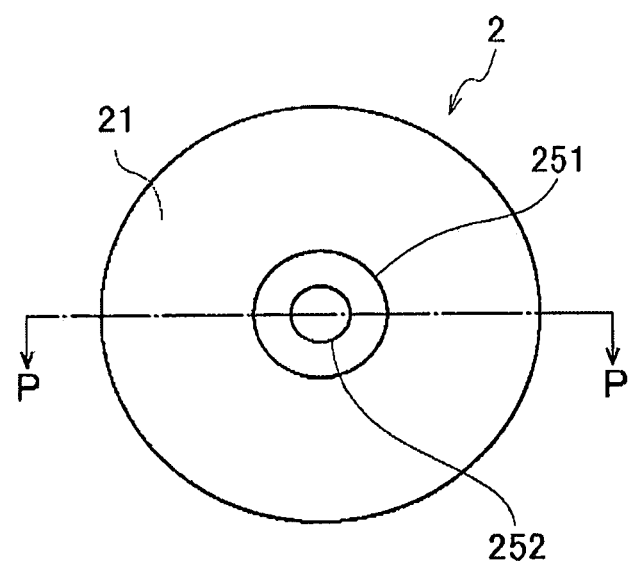
FIG. 14A is a top view and FIG. 14B is a front view of a reference example of the plug used in the present invention.
Figure 14B:
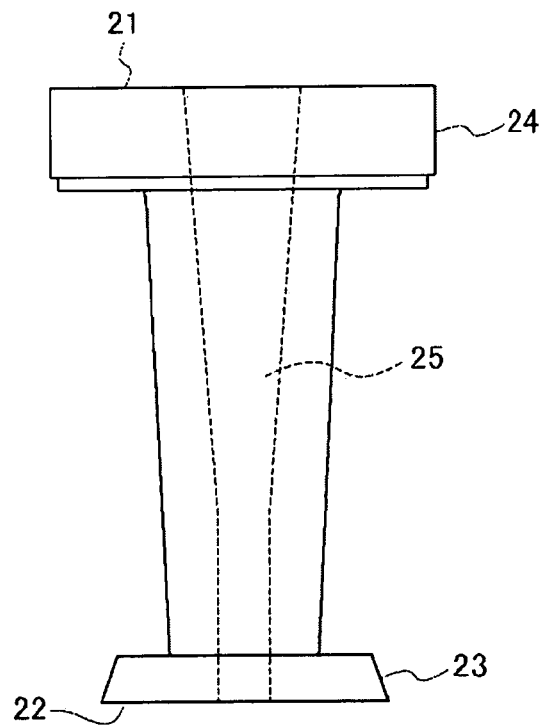
Figure 14C:
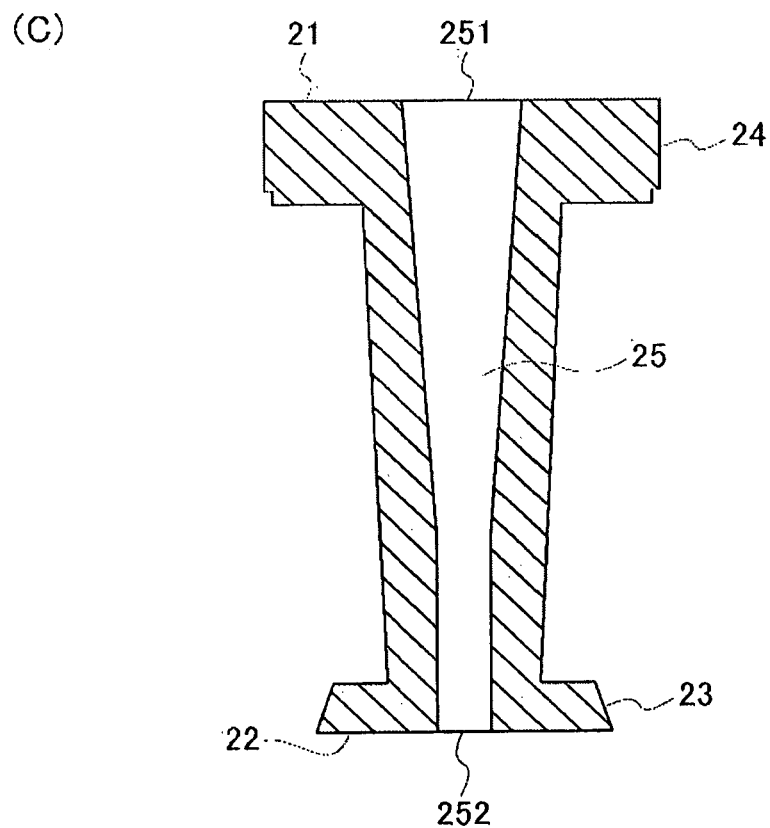
FIG. 14C is a cross-sectional view of the plug illustrated in FIGS. 14A and 14B.

A top view, a front view, and a cross-sectional view of the reference example of the plug used in the present invention are illustrated in FIGS. 14 (A), 14 (B), and 14 (C), respectively. The plug of this reference example is manufactured by 3D printing. When it is assumed that an axis extends in the insertion direction, the shaft section of the plug is gradually tapered in the insertion direction (the direction in which the array is located), and has a tapered shape as a whole. The fringes 23 and 24 are provided at both ends of the plug and the plug has a bobbin structure as a whole. The upper fringe (second fringe 24) of the plug serves as a support section against the array when the plug is inserted into the opening. A thin step is provided on the lower side of the upper fringe, and the step section is brought into fitting engagement with the opening of the array with a round shape and half-fixed by its own weight to the opening of the array so as not to hinder the subsequent series of operations. The plug can be easily inserted into the opening of the array. The step section prevents the solvent discharged into the discharge space from leaking to the outside via the side of the upper fringe.

The mechanical dimensions of an example of a plug that can be fitted to a standard 96-well array are as follows. The upper fringe of the plug has a thin cylindrical shape with an outer diameter of about 8.3 mm, and the thickness of the upper fringe is about 2 mm. The lower fringe (first fringe 23) is formed such that the outer diameter of the lower surface is larger than that of the upper surface and the side surface is slightly tapered. The outer diameter of the lowermost surface of the lower fringe is about 5.9 mm, and the outer diameter of the uppermost surface is about 5.4 mm. The thickness of the lower fringe is about 1 mm. The distance between the lowermost surface of the upper fringe and the uppermost surface of the lower fringe is about 10.9 mm, except for the step section below the upper fringe. The axial length of the entire plug is about 13.9 mm. When the plug in accordance with the present invention is used in a standard 384-well array, the above-mentioned mechanical dimensions should be respectively reduced and specified so as to conform to the dimensions of the opening.

The plug includes a tapered through hole that extends from a center portion of the upper fringe through the center of the shaft section, and the tapered through hole functions as the solvent introduction passage 25 for the first solution, the second solution, or the like. The diameter of the through hole on the upper surface of the upper fringe is about 2.5 mm. The inner diameter of the through hole in the range up to the position (inner diameter change point) with a distance of about 3.8 mm from the lowermost surface of the plug is tapered from the uppermost surface of the upper fringe towards the lowermost surface, so that the through hole as a whole has a tapered shape. The through hole has a cylindrical shape in the range from the above-described inner diameter change point to the lowermost surface of the lower fringe. The hole in the uppermost surface of the upper fringe serves as the inlet 251 for introduction of the solvent or the like and the hole in the lowermost surface of the lower fringe serves as the outlet 252 for introduction of the solvent or the like into the solution introduction space. In the case of the plug of this reference example, the shaft section of the plug is considerably thin as compared with the fringes, and a solvent discharge space having a slightly large volume is created between the plug and the inner wall of the opening of the array, where the solvent discharge space is provided around the shaft section.

Figure 15:
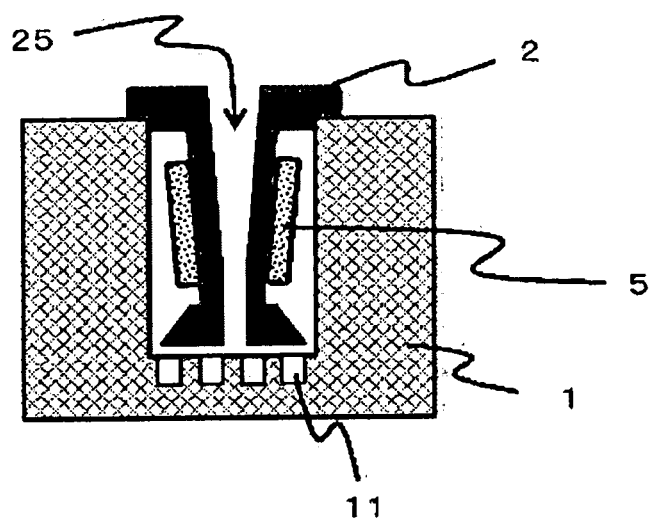
FIG. 15 is a diagram illustrating an adsorbent substance included in the plug used in the present invention.

The plug is inserted into the opening of the array, the plug is brought into fitting engagement with the opening at the step section of the lower portion of the upper fringe and thereby half-fixed thereto. The insertion of the plugs into the openings may be performed one at a time by manual operations or multiple plugs can be simultaneously inserted into the openings using a jig. Also, plugs can be simultaneously inserted into multiple rows or the whole of the 96 wells of the array by a robotic system. If the object to be inspected contains an infectious pathogen, it is preferable to automate the operation of the plugs in order to prevent contamination of the operator and the external environment. In addition, when a solvent including an infectious pathogen is discharged from the solvent introduction space to the discharge space, it will be a problem if the solvent leaks to the outside of the opening of the array. In order to prevent this problem, it is preferable to provide in advance an adsorbent substance 5 outside the shaft section of the plug 2. This is because the solvent that has been discharged from the solution introduction space to the discharge space can be adsorbed thereby (see FIG. 15).

The material of the plug can be a thermoplastic resin or a thermosetting resin that can be easily molded by 3D printing. Polypropylene (PP), ABS resin, polycarbonate, and the like may be mentioned. Also, the plug can also be manufactured by a general-purpose resin injection molding method. Thus, it is preferable that the material of the plug has a predetermined rigidity after molding, is suitable for precision molding, and has predetermined physical properties such as heat resistance, low adsorption, low moisture permeability, and chemical resistance. Also, it is particularly preferable that the use of the plug in pharmaceutical and biomedical applications is approved. For example, cyclic olefin polymers (COPs) are well known for pharmaceutical and biomedical applications. Further, PPSU/PPSF resin which is highly heat resistant and suitable for sterilization is also suitable.

In the present invention, in order to optically detect the number of objects to be inspected contained in the solvent with high accuracy, it is desirable that the plug exhibit light blocking or light absorbing properties at the wavelength of the light in use. In particular, the optical detection is mainly carried out as optical measurement of the object to be inspected within the receptacle from the lower side of the array. Accordingly, it is preferable that the lower fringe of the plug be black. In this reference example, a black thermoplastic resin material is used.

The present invention can adopt an array having typical well numbers and arrangements, such as 96 wells, 384 wells, and the like. The overall shape of the opening is basically flat-bottomed. The surface of the array is planar and suitable for allowing liquid to flow. The shape of the opening in the planar direction of the array is circular and is suitable for capturing a solvent or a bead including the object to be inspected. Also, in order to detect with high precision the solvent or the beads including the captured object to be inspected, it is necessary to measure the entirety of the numerous receptacles provided at the bottom of the opening in a short time. When such optical measurements are carried out, it is important that the background noise, such as unwanted light emitted from the plug or the array as such is low.

Further, the volume of one opening is about 1 to 400 µL. Materials for the array may include resins such as polypropylene, polystyrene, and COP. Amongst these and other resins, it is preferable to use a material suitable for pharmaceutical and biomedical applications. The outer diameter of one opening is about 7 mm and the depth is about 10 to 12 mm. For example, an outer diameter of a well-known array is 126×85×20 mm with a rectangular shape.

Further, the bottom of each opening is provided with minute receptacles. The diameter of the receptacles is about 4 to 8 µm at the surface of the bottom, and typically 5 µm. Also, the depth of one receptacle is about 6 to 12 µm. The volume of one receptacle is of a femtoliter size.

Figure 16:
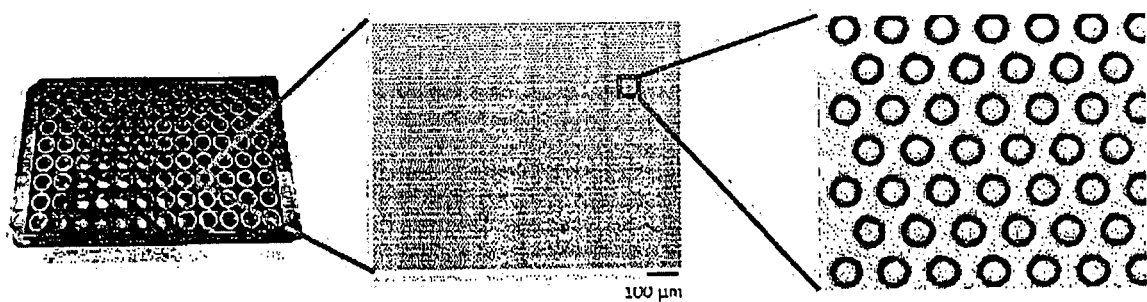
FIG. 16 is a photograph showing a whole picture of a reference example of a 96-well array used in the present invention, a partial enlargement of an opening, and a partial enlargement of receptacles provided at the bottom of the opening.

An example of an 8×16 96-well array that can be used in the present invention will be described. FIG. 16 shows the entire array, a photograph of a partial enlargement of the opening, and a photograph of a partial enlargement of the receptacles provided at the bottom of the opening. A large number of receptacles are geometrically arranged, and hundreds of thousands of receptacles can be arranged per one opening depending on the size (diameter) of the one receptacle and arrangement pitch or arrangement density of the receptacles. In this reference example, the receptacles are provided in a zigzag arrangement where one receptacle in one row is offset by half the size of the receptacle relative to corresponding one of the receptacles belonging to an adjacent row.

Figure 17:
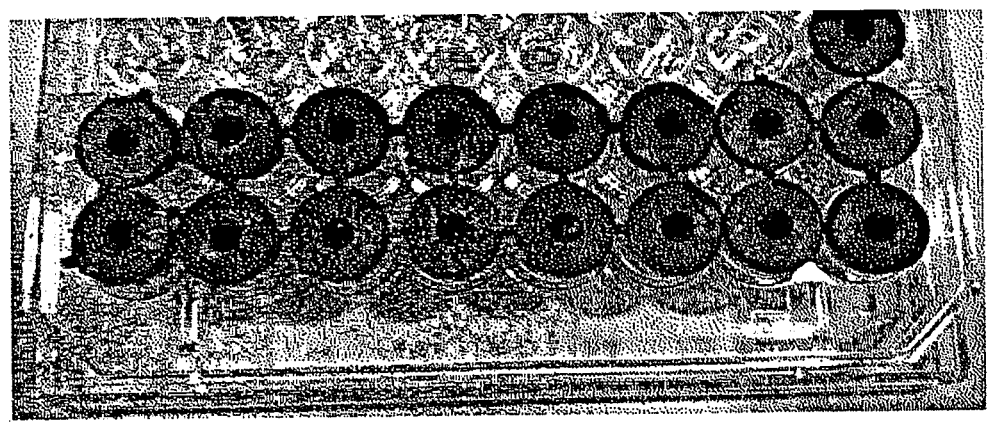
FIG. 17 is a photograph showing a state where one plug or 16 plugs coupled in two rows in advance are inserted in the array.
Figure 18:
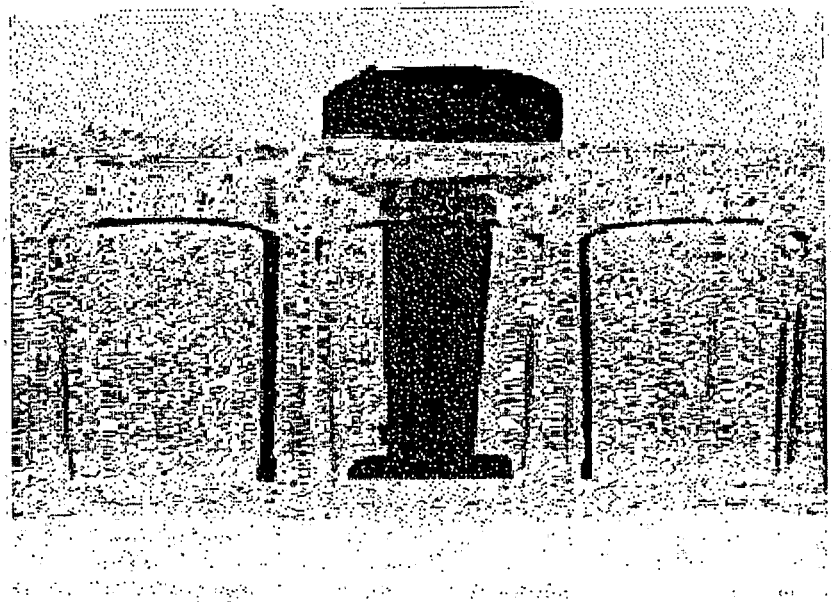
FIG. 18 is a photograph showing a state where one plug is inserted in the array.

In the present invention, plugs can be manually inserted into the array. This is suitable for laboratory experiments and single experiments. Alternatively, 96 plugs can be inserted semi-automatically into 96 holes by using a dedicated device for insertion in combination with manual operation. FIG. 17 illustrates a state where two rows of plugs are connected in advance and 16 plugs as one set are inserted into the array. At the other one location, one plug is manually inserted. FIG. 18 shows a photograph taken from the side of the array with one plug inserted into the opening of the array.

Figure 19:
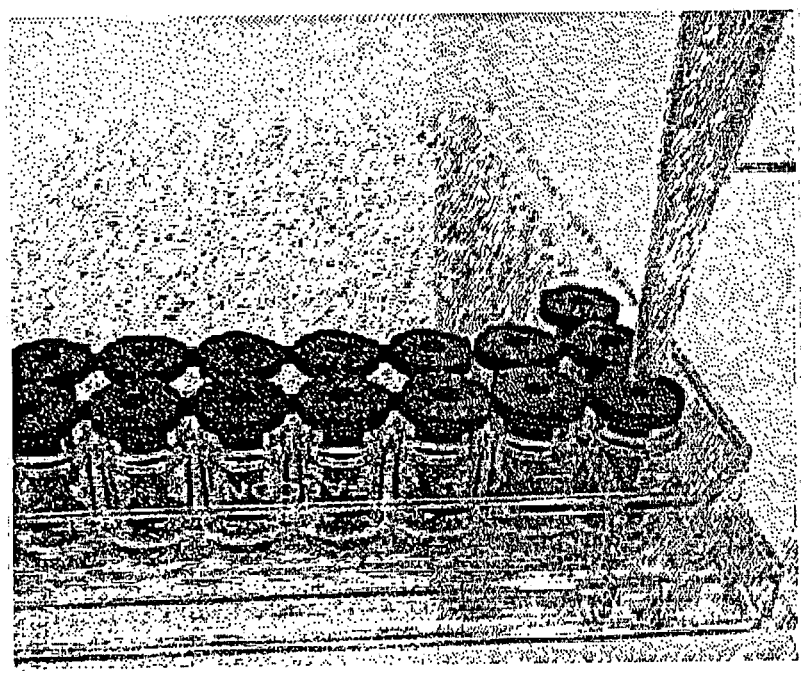
FIG. 19 is a photograph showing a state where a solvent is injected with a pipette via an end of one of the two-rows-coupled plugs inserted in the array.

FIG. 19 is a photograph showing a state where a solvent is injected with a pipette from one end of two connection plugs inserted into the array. The plug, after being inserted into the opening of the array, is supported by the upper fringe of the plug and is rigidly secured to the array, without lateral rocking. Further, the first liquid and then the second liquid are sequentially injected from the inlet provided at the center of the plug. The array may be provided with heating/cooling means as described in Patent Literature 2. Alternatively, it is also possible to construct a robotic system that automatically performs handling of the array and the plug to implement automatic processing.

REFERENCE SIGNS LIST

1: array; 11: well; 11a: solution introduction space; 11b: solution discharge space; 111: receptacle-formed surface; 112: receptacle; 113: sidewall; 114: opening; 2: plug; 21: top surface; 22: bottom surface; 23: first fringe; 231: gap; 232: notch; 24: second fringe; 25: solvent introduction passage; 251: inlet; 252: outlet; 26: projection; 3: target substance; 31: enzyme; 4: chromogenic substrate; 5: adsorbent substance; 6: reaction product; 7: detector; D: droplet; S1: first solution; S2: second solution

The invention claimed is:

1. A method of enclosing a microscopic body in at least some of a plurality of cavities formed, in a surface of a substrate and separated from each other, the method comprising:
   (1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and
   providing a solution discharge space that is in communication with the solution introduction space, the solution discharge space being located
   above the bottom surface of the insertion member, and
   between the substrate and the insertion member, within the substrate, and/or within the insertion member;
   (2) a second step of introducing a first liquid into the solution introduction space, wherein the first liquid includes the microscopic body and a first solvent; and
   (3) a third step of introducing a second liquid into the solution introduction space, wherein the second liquid includes a second solvent immiscible with the first solvent, discharging, into the solution discharge space, the first liquid introduced into the solution introduction space as a portion of the first liquid introduced into the solution introduction space and the cavities, and thereby forming, within the cavities, a droplet of the first liquid coated with the second liquid and containing the microscopic body.

2. The method according to claim 1, wherein, in the first step, the solution discharge space is provided
   (i) above the bottom surface of the insertion member, and between the substrate and the insertion member,
   (ii) above the bottom surface of the insertion member, and within the substrate,
   (iii) above the bottom surface of the insertion member, and between the substrate and the insertion member and within the substrate,
   (iv) above the bottom surface of the insertion member, and within the insertion member, or
   (v) above the bottom surface of the insertion member, and between the substrate and the insertion member and within the insertion member.

3. The method according to claim 2, wherein the insertion member has a bobbin-like shape including fringes at both ends in an insertion direction,
   the bottom surface of the insertion member defines a first fringe having substantially the same shape as that of the cavity-formed surface of the substrate, and
   the first fringe divides an upper space above the cavity-formed surface of the substrate into two spaces, the two spaces including
   the solution introduction space positioned between the first fringe and the cavity-formed surface and
   the solution discharge space positioned above the first fringe.

4. The method according to claim 1, wherein, in the second step, the first liquid is introduced into the solution introduction space via a flow passage formed in the insertion member and/or the substrate and having an outlet in the solution introduction space.

5. The method according to claim 1, further comprising, between the second step and the third step, a step of controlling a temperature of the substrate in which the cavities are formed.

6. A method of enclosing a microscopic body in at least some of a plurality of cavities formed in a surface of a substrate and separated from each other, the method comprising the steps of:
   (A) arranging an insertion member above a cavity-formed surface of the substrate such that a bottom surface of the insertion member and the cavity-formed surface of the substrate face each other, and introducing a first liquid into a solution introduction space thus formed between the bottom surface of the insertion member and the cavity-formed surface of the substrate, wherein the first liquid includes the microscopic body and a first solvent; and
   (B) introducing a second liquid into the solution introduction space, wherein the second liquid includes a second solvent immiscible with the first solvent, discharging the first liquid introduced into the solution introduction space as a portion of the first liquid introduced into the solution introduction space and the cavities into a solution discharge space that is in communication with the solution introduction space, and thereby forming, within the cavities, a droplet of the first liquid coated with the second liquid and containing the microscopic body.

7. A method of detecting a microscopic body enclosed in at least some of a plurality of cavities formed in a surface of a substrate and separated from each other, the method comprising:
   (1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and
   providing a solvent discharge space that is in communication with the solution introduction space, the solvent discharge space being located
   above the bottom surface of the insertion member, and
   between the substrate and the insertion member, within the substrate, and/or within the insertion member;
   (2) a second step of introducing a first liquid into the solution introduction space, wherein the first liquid includes the microscopic body and a first solvent;
   (3) a third step of introducing a second liquid into the solution introduction space, wherein the second liquid includes a second solvent immiscible with the first solvent, discharging, into the solution discharge space, the first liquid introduced into the solution introduction space as a portion of the first liquid introduced into the solution introduction space and the cavities, and thereby forming, within the cavities, a droplet of the first liquid coated with the second liquid and containing the microscopic body; and
   (4) a fourth step of optically, electrically and/or magnetically detecting the microscopic body present in the droplet.

8. A method of optically detecting a microscopic body enclosed in at least some of a plurality of cavities formed in a surface of a substrate and separated from each other, wherein the microscopic body is optically detected on the basis of a change in absorbance and/or fluorescence of a chromogenic substrate, the method comprising:

(1) a first step of arranging an insertion member above a cavity-formed surface of the substrate, determining relative positions of the insertion member and the substrate by a support section provided on the insertion member such that a bottom surface of the insertion member and the cavity-formed surface of the substrate face each other, thereby providing a solution introduction space between the bottom surface of the insertion member and the cavity-formed surface of the substrate, and providing a solvent discharge space that is in communication with the solution introduction space, the solvent discharge space being located above the bottom surface of the insertion member, and between the substrate and the insertion member, within the substrate, and/or within the insertion member;

(2) a second step of introducing a first liquid including the microscopic body, the chromogenic substrate, and a first solvent into the solution introduction space;

(3) a third step of introducing a second liquid into the solution introduction space, wherein the second liquid includes a second solvent immiscible with the first solvent, discharging, into the solution discharge space, the first liquid introduced into the solution introduction space as a portion of the first liquid introduced into the solution introduction space and the cavities, and thereby forming, within the cavities, a droplet of the first liquid coated with the second liquid and containing the microscopic body; and (4) a fourth step of detecting a change in absorbance and/or fluorescence of the chromogenic substrate present in the droplet.

9. A microscopic body detection device comprising:
a substrate including a surface having a plurality of cavities formed therein so as to be separated from each other such that microscopic bodies are enclosed in the cavity; and
an insertion member arranged above a cavity-formed surface of the substrate,
the insertion member including a support section for determining a relative position of the insertion member relative to the substrate,
a solution introduction space being provided between the cavity-formed surface of the substrate and a bottom surface of the insertion member, arranged above the cavity-formed surface to face the cavity-formed surface,
a solution discharge space being provided that is in communication with the solution introduction space, the solution discharge space being provided
above the bottom surface of the insertion member, and
between the substrate and the insertion member, within the substrate, and/or within the insertion member, and
a flow passage being formed in the insertion member and/or the substrate, the flow passage having an outlet in the solution introduction space.

10. The device according to claim 9, wherein a first solvent held in the solution introduction space is substituted by a second solvent that is immiscible with the first solvent, the second solvent being introduced into the solution introduction space via the flow passage, and the substituted first solvent is allowed to be discharged to the solution discharge space.

11. The device according to claim 10, wherein a first liquid held in the solution introduction space as a portion of the first liquid held in the solution introduction space and the cavity and including the microscopic body and the first solvent is discharged to the solution discharge space by a second liquid including the second solvent immiscible with the first solvent and being introduced into the solution introduction space via the flow passage, and a droplet of the first liquid coated with the second liquid and containing the microscopic body is formed in the cavity.

12. The device according to claim 9, wherein the solvent discharge space is provided
(i) above the bottom surface of the insertion member and between the substrate and the insertion member,
(ii) above the bottom surface of the insertion member, and within the substrate,
(iii) above the bottom surface of the insertion member, and between the substrate and the insertion member and within the substrate,
(iv) above the bottom surface of the insertion member, and within the insertion member, or
(v) above the bottom surface of the insertion member, and between the substrate and the insertion member and within the insertion member.

13. The device according to claim 12, wherein the first fringe of the insertion member includes a notch, and
the notch brings the solution introduction space and the solution discharge space into communication with each other such that liquid is allowed to flow when the insertion member is arranged above the cavity-formed surface.

14. The device according to claim 9, wherein the insertion member has a bobbin-like shape including fringes at both ends in an insertion direction,
the bottom surface of the insertion member defines a first fringe having substantially the same shape as that of the cavity-formed surface of the substrate, and
the first fringe divides an upper space above the cavity-formed surface of the substrate into two spaces, the two spaces including
the solution introduction space positioned between the first fringe and the cavity-formed surface and
the solution discharge space positioned above the first fringe.

15. The device according to claim 14, wherein the support section is a second fringe provided at a peripheral portion of an upper end of the insertion member,
the second fringe is brought into locking engagement with the substrate when the insertion member is arranged above the cavity-formed surface of the substrate, and a height of the insertion member from the first fringe to the second fringe defines a height of the solution discharge space.

16. The device according to claim 14, wherein the support section is a projection provided on the bottom surface of the insertion member, and a height of the projection defines a height of the solution introduction space.

17. The device according to claim 14, wherein a gap created between the first fringe and the substrate brings the solution introduction space and the solution discharge space into communication with each other such that liquid is allowed to flow when the insertion member is arranged above the cavity-formed surface.

18. The device according to claim 9, wherein the insertion member has a property of not allowing light to pass therethrough at least at its bottom surface.

19. The device according to claim 9, wherein the support section is brought into fitting engagement with the substrate when the insertion member is arranged above the cavity-formed surface of the substrate.

20. The device according to claim 9, further comprising a temperature controller that controls a temperature of the substrate.

21. The device according to claim 9, further comprising a detector that optically, electrically, and/or magnetically detects the microscopic body present in the cavity.

* * * * *